(12) United States Patent
Iasemidis et al.

(10) Patent No.: US 6,304,775 B1
(45) Date of Patent: Oct. 16, 2001

(54) SEIZURE WARNING AND PREDICTION

(76) Inventors: Leonidas D. Iasemidis, 4719 SW. 88th Dr.; James Chris Sackellares, 5404 SW. 91st Ter., both of Gainesville, FL (US) 32608

( * ) Notice: Subject to any disclaimer, the term of this patent is extended or adjusted under 35 U.S.C. 154(b) by 0 days.

(21) Appl. No.: 09/400,982

(22) Filed: Sep. 22, 1999

(51) Int. Cl.⁷ .................................................. A61B 5/04

(52) U.S. Cl. ............................................................ 600/544

(58) Field of Search .................................... 600/544, 378, 600/300, 545; 607/45; 364/574

(56) References Cited

U.S. PATENT DOCUMENTS

| | | |
|---|---|---|
| 3,850,161 | 11/1974 | Liss . |
| 3,863,625 | 2/1975 | Viglione et al. . |
| 4,987,680 | 1/1991 | Sofia . |
| 5,082,861 | 1/1992 | Sofia . |
| 5,292,772 | 3/1994 | Sofia . |
| 5,311,876 * | 5/1994 | Olsen et al. ........................... 600/544 |
| 5,349,962 * | 9/1994 | Lockard et al. ....................... 600/544 |
| 5,743,860 * | 4/1998 | Hively et al. .......................... 600/544 |
| 5,815,413 * | 9/1998 | Hively et al. .......................... 364/574 |
| 5,857,978 * | 1/1999 | Hively et al. .......................... 600/544 |
| 5,938,689 * | 8/1999 | Fischell et al. ........................ 600/544 |
| 5,995,868 * | 11/1999 | Dorfmeister et al. ................. 600/544 |

OTHER PUBLICATIONS

L. Isaemidis et al., "Automated Seizure Prediction Paradigm", Epilepsia, vol. 39, pp. 56, 1998.

J. Sackellares et al., "Epileptic Seizures as Neural Resetting Mechanisms", Epilepsia, vol. 38, Sup. 3, 1997.

L. Iasemidis et al., "Epileptogenic Focus Localization by Dynamical Analysis of Interictal Periods of EEG in Patients with Temporal Lobe Epilepsy", Epilepsia, vol. 38, suppl. 8, pp. 213, 1997.

L. Iasemidis et al., "Dynamical Interaction of the Epileptogenic Focus with Extrafocal Sites in Temporal Lobe Epilepsy (TLE)", Ann. Neurol., vol. 42, pp. 429, 1997.

L. Iasemidis et al., "Preictal Entrainment of a Critical Cortical Mass is a Necessary Condition for Seizure Occurrence", Epilepsia, vol. 37, suppl. 5, 1996.

M. C. Cadagli, et al., "Nonlinear Analysis of Mesial Temporal Lobe Seizures Using a Surrogate Data Technique", Epilepsia, vol. 36, suppl. 4, pp. 142, 1995.

J. Sackellares et al., "Dynamical Studies of Human Hippocampus in Limbic Epilepsy", Neurology, vo. 45, Suppl. 4, pp. A 404, 1995.

L. Iasemidis et al., "Spatiotemporal Evolution of Dynamical Measures Precedes Onset of Mesial Temporal Lobe Seizures", Epilepsia, vol. 358, pp. 133, 1994.

L. Iasemidis et al., "Time Dependencies in Partial Epilepsy", vol. 34, pp. 130–131, 1993.

(List continued on next page.)

Primary Examiner—John P. Lacyk
Assistant Examiner—Brian Szmal
(74) Attorney, Agent, or Firm—Burns, Doane, Swecker & Mathis, L.L.P.

(57) ABSTRACT

Impending seizure warning (ISW), seizure susceptibility period detection (SSPD), hours or days before an impending seizure, and time to impending seizure prediction (TISP) are provided by measuring each of a number of signals from different locations about a patient's brain, and generating therefrom, a spatio-temporal response based on these signals. Chaoticity profiles are then generated for each spatio-temporal response. Over a period of time, a determination is made as to whether a certain level of dynamic entrainment exists between the chaoticity profiles associated with the responses from a set of critical locations. If so, a seizure warning, an indication of seizure susceptibility and a prediction of a time of occurrence of an impending seizure may be issued.

47 Claims, 13 Drawing Sheets

OTHER PUBLICATIONS

Hitten P. Zaveri et al., "Time–Frequency Analyses of Non-stationary Brain Signals", Electroencephalography and Clinical Neurophysiology, vol. 79, pp. 28P, 1991.

L. Iasemidis et al., "Localizing Preictal Temporal Lobe Spike Foci Using Phase Space Analysis", Electroencephalography and Clinical Neurophysiology, vol. 75, pp. 63–64, 1990.

J. Sackellares et al., "Measurement of Chaos to Localize Seizure Onset", Epilepsia, vol. 30, No. 5, 1989.

Philip Schwartzkroin, "Origins of the Epileptic State", Epilepsia, vol. 38, suppl. 8, pp. 853–858, 1997.

Thomas Elbert et al., "Chaos and Physiology: Deterministic Chaos in Excitable Cell Assemblies", Physiological Reviews, vol. 74, No. 1, Jan. 1994.

Martin Casdagli et al., "Non–Linearity in Invasive EEG Recordings from Patients with Temporal Lobe Epilepsy", Electroencephalography and Clinical Neurophysiology, vol. 102, pp. 98–105, 1997.

L. Iasemidis et al., "Phase Space Topography and the Lyapunov Exponent of Electrocorticograms in Partial Seizures", Brain Topography, vol. 2, No. 3, 1990.

L. Iasemidis et al., "Time Dependencies in the Occurrences of Epileptic Seizures", Epilepsy Research, vol. 17, pp. 81–94, 1994.

L. Iasemidis et al., "The Evolution with Time of the Spatial Distribution of the Largest Lyapunov Exponent on the Human Epileptic Cortex", World Scientific, 1991.

M.C. Casdagli et al., "Characterizing Nonlinearity in Invasive EEG Recordings from Temporal Lobe Epilepsy", Physica D 99, pp. 381–399, 1996.

L. Iasemidis et al., "Chaos Theory and Epilepsy" The Neuroscientist, pp. 118–126, 1996.

L. Iasemidis et al., "Quantification of Hidden Time Dependencies in the EEG Within the Framework of Nonlinear Dynamics", World Scientific, pp. 30–47, 1993.

F.L. Silva, "Spatiotemporal Models in Biological and Artifical Systems", Ohmsha IOS Press, vol. 37, pp. 81–88, 1997.

L. Iasemidis et al., "Modelling of EcoG in Temporal Lobe Epilepsy", Proceedings of the $25^{th}$ Rocky Mountain Bioengineering Symposium, pp. 187–193, 1988.

L. Iasemidis et al., "Spatiotemporal Dynamics of Human Epileptic Seizures", Proceedings of the $3^{rd}$ Experimental Chaos Conference, World Scientific, pp. 26–30, 1996.

L. Iasemidis et al., "Measurement and Quantification of Spatio–Temporal Dynamics of Human Epileptic Seizures", Nonlinear Signal Processing in Medicine, IEEE Press, pp. 1–27, 1999.

L. Iasemidis et al., "Spatiotemporal Transition to Epileptic Seizures: A Nonlinear Dynamical Analysis of Scalp and Intracranial EEG Recordings", Proceedings of Spatiotemporal Models in Biological and Artifical Systems, pp. 1–8, 1996.

Philip Schwartzkroin, "Origins of the Epileptic State", Epilepsia, vol. 38, Supp. 8, pp. 853–858, 1997.

L. Isaemidis et al., "Preictal–Postictal Versus Postictal Analysis for Epileptogenic Focus Localization", J. Clin. Neurophysiol, vol. 14, pp. 144, 1997.

L. Iasemidis et al., "Detection of the Preictal Transition State in Scalp–Sphenoidal EEG Recordings", American Clinical Neurophysiology Society Annual Meeting, Sep. 1996.

J. Sackellares et al. "Relationship Between Hipppocampal Atrophy and Dynamical Measures of EEG in Depth Electrode Recordings", American Electroencephalographic Society Annual Meeting, Sep. 1995.

J. Sackellares et al., "Computer–Assisted Seizure Detection Based on Quantitative Dynamical Measures", American Electroencephalographic Society Annual Meeting, Sep. 1994.

L. Iasemidis et al., "The Use of Dynamical Analysis of EEG Frequency Content in Seizure Prediction", American Electroencephalographic Society Annual Meeting, Oct. 1993.

L. Iasemidis et al., "Long–Time–Scale Temporo–spatial Patterns of Entrainment of Preictal Electrocorticographic Data in Human Temporal Lobe Epilepsy", Epilepsia, vol. 31, No. 5, 1990.

L. Iasemidis et al., "Nonlinear Dynamics of EcoG Data in Temporal Lobe Epilepsy", Electroencephalography and Clinical Neurophysiology, vol. 5, pp. 339, 1998.

* cited by examiner

SEIZURE WARNING AND PREDICTION

STATEMENT REGARDING FEDERALLY SPONSORED RESEARCH AND DEVELOPMENT

The research and development effort associated with the subject matter of this patent application was support by the National Institutes of Health under grant no. R01 NS31451.

FIELD OF INVENTION

The present invention involves the field of signal processing. More particularly, the present invention involves the processing of electrical and/or electromagnetic signals generated by the brain.

BACKGROUND

Epilepsy is a chronic disorder characterized by recurrent brain dysfunction caused by paroxysmal electrical discharges in the cerebral cortex. If untreated, an individual afflicted with epilepsy is likely to experience repeated seizures, which typically involve some level of impaired consciousness. Some forms of epilepsy can be successfully treated through medical therapy. However, medical therapy is less effective with other forms of epilepsy, including Temporal Lobe Epilepsy (TLE) and Frontal Lobe Epilepsy (FLE). With TLE and FLE, removing the portion of the hippocampus and/or cerebral cortex responsible for initiating the paroxysmal electrical discharges, known as the epileptogenic focus, is sometimes performed in an effort to control the seizures.

For quite some time, a few investigators in the medical research community have attempted to develop techniques which effectively provide seizure prediction and/or seizure warning, where seizure prediction will be understood to involve long-range forecasting of seizure-onset time, whereas seizure warning will be understood to involve long-range indications of conditions conducive to an impending seizure. As one skilled in the art will surely appreciate, any such technique would have numerous clinical as well as non-clinical applications. For example, in order to more effectively treat patients that are resistant to conventional medical therapy, such a technique might be used in conjunction with a device, perhaps an implanted device, designed to deliver a dosage of anti-seizure medication into the patient's bloodstream for the purpose of averting an impending seizure.

In another example, such a technique could be used during pre-surgical evaluations to assist in pinpointing the epileptogenic focus, which is to be removed during surgery. It is understood that during a seizure, blood flow to the epileptogenic focus significantly increases. If certain radio-labeled ligands are injected into the patient's bloodstream in a timely manner, it is possible to monitor that increased blood flow using radiography, thereby allowing a physician to accurately pinpoint the boundaries of the epileptogenic focus. A true seizure prediction and/or warning technique would, ideally, provide an indication of an impending seizure well in advance so as to provide sufficient time to prepare for and administer, for example, the aforementioned radiography ligand.

The most important tool for evaluating the physiological states of the brain is the electroencephalogram (EEG). The standard for analysis and interpretation of the EEG is visual inspection of the graphic tracing of the EEG by a trained clinical electroencephalographer. There is no established method for predicting seizure onset by visual analysis of the EEG. Traditional signal processing techniques yield little practical information about the EEG signal. Such methods, however, are limited in their effectiveness because the brain is a multidimensional system that produces nonlinear signals and exhibits spatial as well as temporal properties.

Moreover, signal processing techniques that simply employ standard, linear, time series analysis methods cannot possibly detect the spatio-temporal properties that are critical in providing effective seizure warning.

To date, there are no known linear or non-linear techniques capable of providing seizure detection, warning, or the like, in advance of seizure onset. At best, present techniques provide, with less than desirable accuracy, seizure detection during the very early stages of a seizure discharge in the EEG (i.e., a few seconds after the initial discharge). The onset of the seizure discharge in the EEG may precede the clinical manifestations (e.g., behavioral and neuromotor responses) of the seizure by up to several seconds, particularly where intra-cranial electrodes are employed for EEG recordings. Because the EEG manifestation may be detected just a few seconds prior to the clinical manifestations of the seizure, some investigators have claimed the ability to predict seizures through evaluation of the EEG. Osorio et al., "Real-time Automated Detection and Quantitative Analysis of Seizures and Short-term Prediction of Clinical Onset," Epilepsia, vol. 39, pp. 615–627, 1998. Such claims are misleading since these techniques simply detect the EEG manifestation of the seizure. These techniques do not, however, provide seizure prediction. Unfortunately, the few seconds afforded by these early seizure detection techniques are insufficient to support practical applications such as the medical intervention therapy and in-patient applications mentioned previously. For example, with respect to employing a seizure detection/warning technique for medical intervention therapy, seizure detection/warnings that precede seizure onset by 5, 10 or even 60 seconds are unlikely to offer any benefit because any medication administered at that time would not have time to reach a sufficient brain concentration to prevent an impending seizure. Even techniques that may be capable of detecting and/or generating seizure warnings no more than a few minutes prior to seizure onset may not support such a treatment. Also, with regard to utilizing a seizure detection/warning technique to support various in-patient applications, present techniques cannot consistently and accurately provide the timely seizure detection/warnings needed to alert medical staff members so they can properly observe the impending seizure, administer medication to avoid the seizure, or prepare for and perform any pre-surgical procedures such as the radiography procedure described above.

A few of the more recently developed techniques have gone beyond simple, linear, time series analysis in an attempt to provide more timely and more accurate seizure detection/warning capabilities. In accordance with one of these most recent techniques, signals from one or more EEG channels are sampled over relatively short time intervals. A high dimensional state space plot is then generated from each channel, using a common technique called the "Method of Delays." A more detailed explanation of the Method of Delays can be found in L. Iasemidis et al., "Quantification of Hidden Time Dependencies in the EEG within the Framework of Nonlinear Dynamics", in Nonlinear Dynamical Analysis of the EEG, eds. B. H. Jansen & M. E. Brandt (World Scientific, Singapore, 1993), pp. 30–47. See also, F. Takens, "Detecting Strange Attractors in Turbulence", in Lec. Notes Math., eds. D. A. Rand & L. S. Young (Springer-Verlag, 1980), 898, pp. 366–381; and H. Whitney, "Differentiable Manifolds", Ann. Math., 37 (1936), pp. 645–680. Each state space plot, in turn, is used to derive correlation integrals for the corresponding signal, where the correlation integrals reflect the complexity (e.g., the correlation dimension, predictability indices) associated with the corresponding signal. A significant drop in the correlation integral values or the correlation dimension (i.e., a reduction in complexity) over time at specific brain sites can be used to trigger an impending seizure warning. See J. Martinerie et al., "Epileptic Seizures can be Anticipated by Nonlinear Analysis", Nature Medicine, vol. 4, pp. 1173–1176, 1998. See also, C. E. Elger et al., "Seizure Prediction by Nonlinear Time Series Analysis of Brain Electrical Activity," European Journal of Neuroscience, vol. 10, pp. 786–789, 1998.

There are numerous deficiencies associated with the above-identified technique. For instance, the estimated measure of signal complexity is unreliable, as it depends on the brain state, and segments without epileptiform activity are arbitrarily selected as reference states. It also depends on which of numerous electrode sites are involved in estimating signal complexity. Furthermore, this technique provides no method for properly selecting brain sites. Also, the threshold used to trigger an impending seizure warning is arbitrary and not adaptive. Accordingly, this technique provides little if any practical utility.

Another technique which employs non-linear methods is described in U.S. Pat. No. 5,857,978 ("Hively et al."). According to the Hively patent, epileptic seizures can be predicted by acquiring brain wave data (e.g., EEG or MEG data) from a patient. The data signals are then digitized and, thereafter, various nonlinear techniques are applied to each signal in order to produce non-linear measures for each signal during short, consecutive time intervals. These measures associated with each signal are then compared to a "known seizure predictor".

There are a number of problems associated with the technique described in the Hively patent. First, the non-linear techniques employed in the Hively patent can only detect and quantify changes in EEG or MEG signal dynamics that occur during the preictal transition period, just prior to seizure onset. The existence of these changes has been known for quite some time. L. Iasemidis et al., "Non-Linear Dynamics of ECoG Data in Temporal Lobe Epilepsy", Electroencephalography and Clinical Neurophysiology, vol. 5, p. 339 (1988). The mere detection of these changes does not constitute true seizure prediction.

Second, in order to provide true seizure prediction capability, an exact range of conditions needs to be defined, such that, when these conditions are met, a seizure prediction can be issued with some level of certainty. The Hively patent does not define this information, nor does it describe any technique whereby such information can be determined. The Hively patent merely monitors certain "seizure indicators" such as abrupt increases, peaks and valleys associated with the EEG or MEG signals. No specific values for these "indicators" are defined. One reason for not doing so is that the values associated with these "indicators" change from patient to patient, and from seizure to seizure, as the data in Table 1 and Table 2 of the Hively patent suggests. Thus, no true seizure prediction technique can reasonably rely on such "indicators."

Third, the Hively patent suggests comparing the "indicators" to "known seizure predictors." However, to date no true seizure predictors are known.

Given the preceding discussion, it is clear that no technique or device to date is capable of providing true seizure prediction and/or warning. However, such a technique or device would be of tremendous interest and importance, not only to those afflicted with seizure disorders, but also to those members of the medical community who are committed to providing care and effective treatment for those who suffer from epileptic seizure related conditions.

SUMMARY OF THE INVENTION

The spatio-temporal characteristics exhibited by certain sites within the brain, when compared with the spatio-temporal, physiological characteristics exhibited by other sites within the brain, are noticeably different prior to an impending seizure as compared to the spatio-temporal characteristics exhibited by these sites during seizure free intervals. As will be discussed in greater detail below, it has been discovered that these spatio-temporal characteristics are noticeably different hours, and in some cases, days before the occurrence of a seizure. As such, the present invention uses these differences as a seizure transition indicator for individual patients.

More particularly, the present invention involves a technique in which these critical, spatio-temporal characteristic changes are quantified for the purpose of providing impending seizure warnings (ISW), seizure susceptibility period detection (SSPD) hours or days before the impending seizure, and estimated time to impending seizure prediction (TISP). In quantifying these spatio-temporal characteristic changes, the present invention, in contrast with the above-identified prior techniques, depends heavily on sequential estimates of the short-term largest Lyapunov exponent, which reflects a measure of chaoticity associated with the behavior of a corresponding electrode site. Also, in contrast with the majority of the above-identified prior techniques, the present invention utilizes sequential comparisons of dynamic measures between two (2) or more electrode sites (i.e., signal channels).

Accordingly, it is an objective of the present invention to provide impending seizure warnings well in advance of seizure onset.

It is also an objective of the present invention to provide seizure susceptibility period detection, hours, if not days before seizure onset.

It is yet another objective of the present invention to accurately predict the amount of time before seizure onset, particularly after issuance of an impending seizure warning.

It is still another objective of the present invention to utilize the ISW, SSPD and TISP features of the present invention in conjunction with seizure intervention techniques, such as anti-seizure drug medication intervention therapy and neuro-stimulation therapy.

It is another objective of the present invention to utilize the ISW, SSPD and TISP features of the present invention in conjunction with various in-patient applications, including pre-surgical evaluation and diagnosis procedures.

In accordance with a first aspect of the present invention, the above-identified and other objects are achieved through a method of analyzing a multidimensional system. This method involves measuring each of a plurality of signals generated by the multidimensional system, where each of the plurality of signals represents a response associated with a corresponding spatial location within the multidimensional system. A phase space representation for each of the plurality of signals is then generated. After generating a phase space representation for each of the plurality of signals, a signal profile is derived for each of the plurality of signals, where each signal profile represents a level of chaoticity for each corresponding signal over time. Each of the signal profiles is then compared, and one or more groups of signals are selected, based on the comparison between their corresponding signal profiles. Ultimately, the state dynamics of the multidimensional system are characterized as a function of the signal profile comparisons associated with the selected one or more signal groups.

In accordance with a second aspect of the present invention, the above-identified and other objects are achieved through a method which provides seizure warning and prediction. The method involves acquiring a time series signal from each of a plurality of locations about the brain, where each signal and its corresponding location constitute a corresponding channel. Then, for each channel, a spatio-temporal response is generated, based on the corresponding time series signal. The method then involves quantifying a sequence of chaoticity values for each channel based on the corresponding spatio-temporal response, where each sequence of chaoticity values constitutes a chaoticity profile. Over time, the chaoticity profiles associated with each of a number of channel pairs are compared, and the levels of entrainment between the chaoticity profiles associated with each of the channel pairs are evaluated. Next, it is determined whether the levels of entrainment associated with one or more of the channel pairs are statistically significant; and, if it is determined that the levels of entrainment associated with one or more of the channel pairs are statistically significant, a seizure warning is generated.

In accordance with a third aspect of the present invention, the above-identified and other objects are achieved through a method of activating a seizure interdiction device. This method involves acquiring each of a plurality of signals from a corresponding location of a patient's brain, where each signal constitutes a separate channel. Then, for each channel, a spatio-temporal response is generated, based on the corresponding signal. The method also involves generating a chaoticity profile, comprising a sequence of chaoticity values, for each channel based on the corresponding spatio-temporal response. Next, it is determined whether a level of entrainment between chaoticity profiles associated with a critical channel pair is statistically significant. If it is determined that the level of entrainment associated with the critical channel pair is statistically significant, a seizure warning is generated, and the seizure interdiction device is triggered to deliver an antiseizure treatment to the patient.

In accordance with a fourth aspect of the present invention, the above-identified and other objects are achieved through an apparatus that provides seizure interdiction. The apparatus includes a plurality of sensors coupled to a patient's head, where the sensors detect signals from a corresponding location of the patient's brain. The apparatus also includes processing means for generating a seizure warning based on the plurality of signals detected by the plurality of sensors, where the processing means comprises: means for receiving the plurality of signals detected by the plurality of sensors; means for preprocessing the plurality of signals detected by the sensors so as to produce a digital equivalent for each of the signals; means for generating a spatio-temporal response for each of a corresponding one of the plurality of digital signals; means for generating a chaoticity profile, comprising a sequence of chaoticity values from each spatio-temporal response; means for determining whether a level of entrainment between chaoticity profiles associated with a critical pair of signals is statistically significant; and means for generating a seizure warning if it is determined that the level of entrainment associated with the critical signal pair is statistically significant. Finally, the apparatus includes a seizure interdiction device coupled to the above-identified processing means, where the seizure interdiction device comprises means for delivering an antiseizure treatment to the patient if a seizure warning is generated.

BRIEF DESCRIPTION OF THE FIGURES

The objects and advantages of the present invention will be understood by reading the following detailed description in conjunction with the drawings in which.

DETAILED DESCRIPTION OF THE INVENTION

Figure 1:
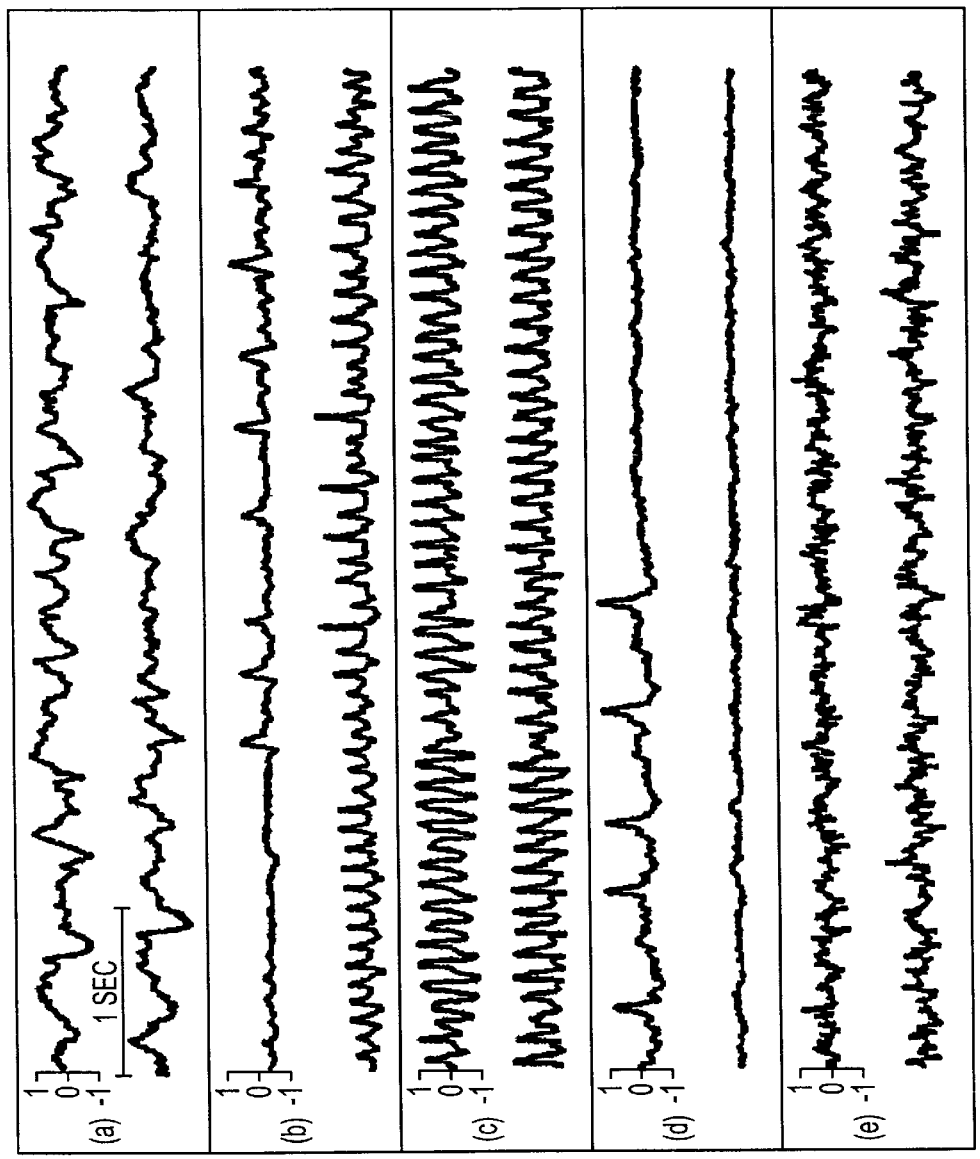
FIGS. 1(a)–(e) illustrates an exemplary, single channel EEG signal as a patient transitions through the various stages of an epileptic seizure.

Seizures, such as epileptic seizures, are multiple stage events. The various stages include a preictal stage, an ictal stage, a postictal stage and an interictal stage. FIGs. 1(a–e) illustrate an exemplary electroencephalogram (EEG) signal, recorded from an electrode overlying an epileptogenic focus, as a patient transitions through the various stages of an epileptic seizure. More specifically, FIG. 1(a) illustrates a time sequence of the EEG signal during the preictal stage, which represents the period of time preceding seizure onset. FIG. 1(b) illustrates a time sequence of the EEG signal during the transition period between the preictal stage and the ictal stage, that includes the seizure onset. It follows that FIG. 1(c) then reflects the EEG signal during the ictal stage, that is within the epileptic seizure, where the ictal stage begins at seizure onset and lasts until the seizure ends. FIG. 1(d), like FIG. 1(b), covers a transitional period. In this case, FIG. 1(d) illustrates a time sequence of the EEG signal during the transition from the ictal stage to the postictal stage, and includes the seizure's end. FIG. 1(e) then illustrates the EEG signal during the postictal stage, where the postictal stage covers the time period immediately following the end of the seizure.

As stated, the preictal stage represents a period of time preceding seizure onset. More importantly, however, the preictal stage represents a time period during which the brain undergoes a dynamic transition from a state of spatio-temporal chaos to a state of spatial order and reduced temporal chaos. Although it will be explained in greater detail below, this dynamic transition during the preictal stage is characterized by dynamic entrainment of spatio-temporal responses associated with various cortical sites. More particularly, the dynamic entrainment of the spatio-temporal responses at these various cortical sites can be further characterized by:

(1) the progressive convergence (i.e., entrainment) of the maximum Lyapunov exponent values (i.e., Lmax) corresponding to each of the various, afore-mentioned cortical sites, wherein Lmax, as one skilled in the art will readily appreciate, provides a measure of chaoticity associated with the spatio-temporal response of a corresponding cortical site; and (2) the progressive phase locking (i.e., phase entrainment) of the Lmax profiles associated with the various cortical sites.

It will be understood, however, that other measures of dynamic entrainment of the chaoticity profiles may be applied (e.g., among first or second or higher order derivatives of the Lmax profiles).

As one skilled in the art will readily appreciate, an EEG signal, such as any of the EEG signals depicted in FIGs. 1(a–e), is a time series that represents a temporal response associated with the spatio-temporal interactions of a particular portion of the brain where the corresponding electrode happens to be located. Since, the brain is a complex, multidimensional system, EEG signals, and other known equivalents, do not and cannot visibly reflect the true spatio-temporal characteristics exhibited by the brain. Thus, traditional linear and nonlinear methods of processing EEG signals for the purpose of providing seizure prediction and/or warning have proven to be generally ineffective as the critical spatio-temporal characteristics exhibited by the brain during the preictal stage cannot be detected from EEG signals. Yet, these critical spatio-temporal characteristics exist long before seizure onset, in some cases, days before seizure onset. As such, these spatio-temporal characteristics exhibited by the brain during the preictal stage are essential to any true seizure prediction scheme.

Figure 2:
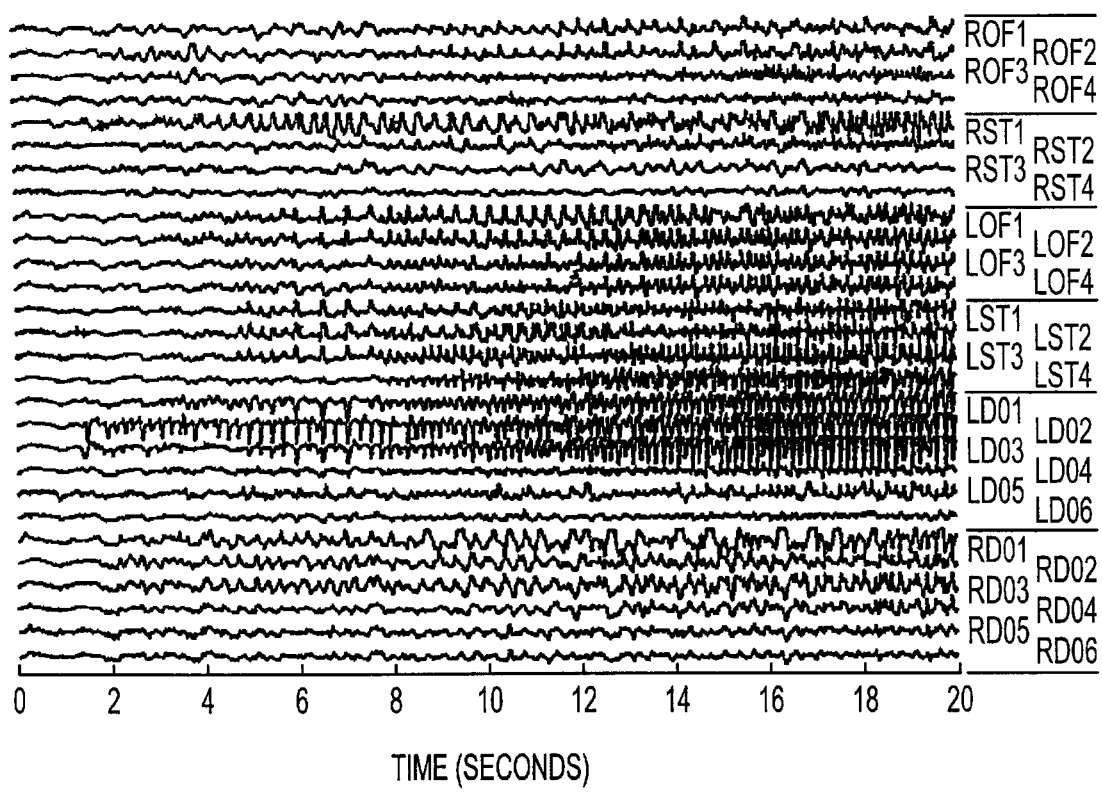
FIG. 2 illustrates a typical, continuous multichannel EEG segment prior to and during seizure onset.

To better illustrate the deficiency of EEG signals, FIG. 2 shows a 20 second EEG segment covering the onset of a left temporal lobe seizure. The EEG segment of FIG. 2 was recorded referentially to linked ears from 12 bilaterally placed hippocampal depth electrodes (i.e., electrodes LDO1–LDO6 and RDO1–RDO6), 8 subdural temporal electrodes (i.e., electrodes RST1–RST4 and LST1–LST4), and 8 subdural orbitofrontal electrodes (i.e., electrodes ROF1–ROF4 and LOF1–LOF4). Seizure onset begins approximately 1.5 seconds into the EEG segment as a series of high amplitude, sharp and slow wave complexes in the left depth electrodes, particularly in LDO1–LDO3, though most prominently in LDO2. With a matter of seconds, the seizure spreads to right subdural temporal electrode RST1, and then to the right depth electrodes RDO1–RDO3. Of particularly importance is the fact that the EEG signals appear normal prior to seizure onset approximately 1.5 seconds into the EEG segment.

The present invention involves a technique that provides early, impending seizure warnings (ISW). The present invention provides this early ISW by focusing on the afore-mentioned, critical spatio-temporal changes that occur during the preictal stage. Moreover, the present invention provides this capability even though the EEG would not manifest any indications of an impending seizure during the preictal stage, as illustrated in FIG. 2. However, in addition to providing an ISW, the present invention is also capable of providing a seizure susceptibility period detection (SSPD), that is, the presence of abnormal brain activity long before the occurrence of a seizure, for example, during an interictal period days before a seizure. Furthermore, the present invention is capable of providing a time to impending seizure prediction (TISP), wherein the TISP reflects an amount of time that is expected to elapse before seizure onset.

Figure 3:
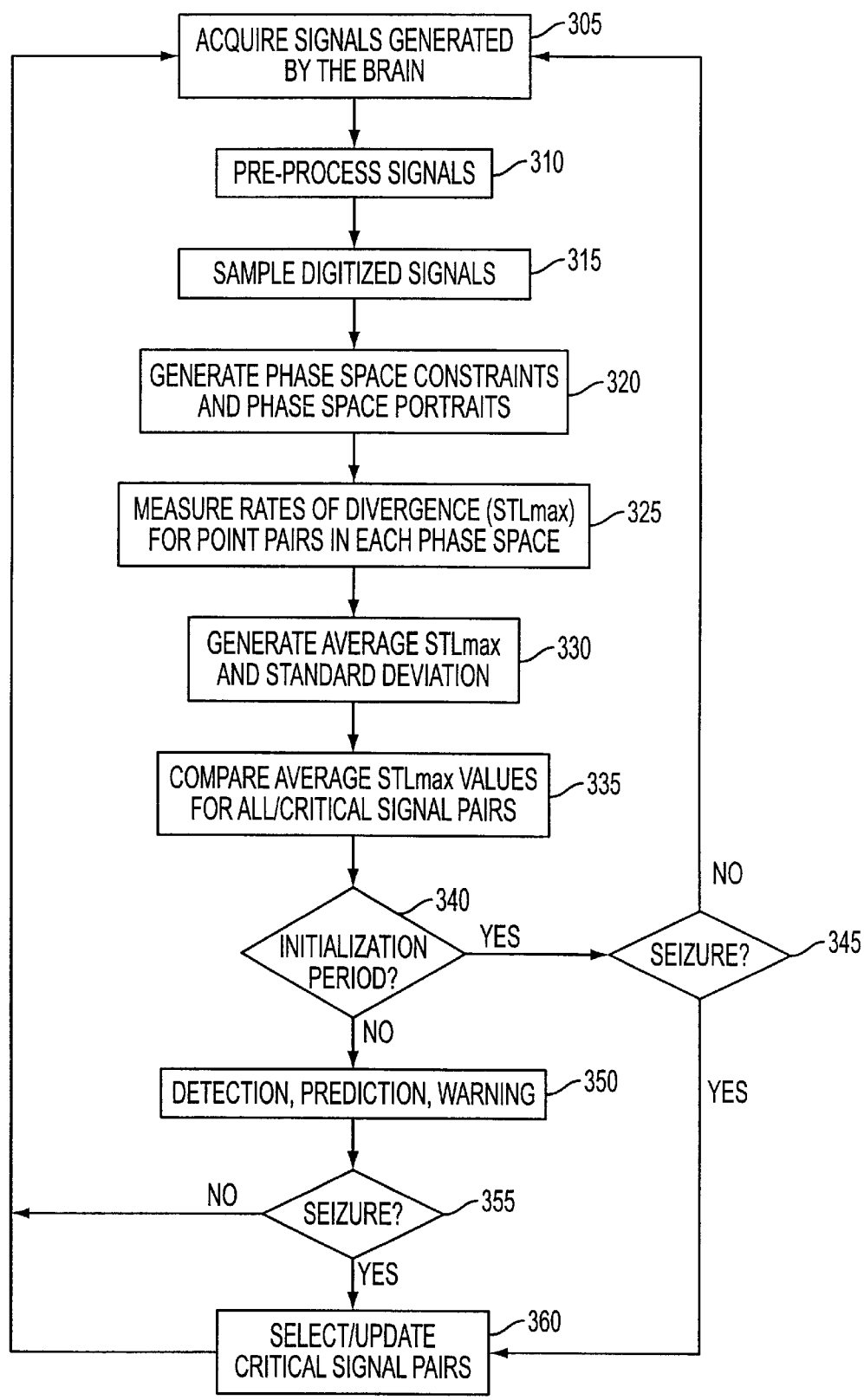
FIG. 3 is a flowchart depicting a procedure for providing early ISW, SSPD and TISP in accordance with exemplary embodiments of the present invention.

FIG. 3 is a flowchart that depicts a procedure for providing early ISW, SSPD, and TISP, in accordance with exemplary embodiments of the present invention. As illustrated, the procedure initially involves acquiring electrical or electromagnetic signals generated by the brain, in accordance with procedural step 305. Each of these signals may, for example, correspond to a single EEG channel, as one skilled in the art will readily appreciate. Each signal is then preprocessed, as shown in procedural step 310, where preprocessing typically includes signal amplification, filtering and digitization. Each of the digitized signals is then sampled, as illustrated in procedural step 315, so as to produce a set of successive samples (i.e., an epoch). During procedural step 320, the samples are used to generate a phase space portrait for each signal epoch. As each of the phase space portraits is being generated, the rate of divergence of adjacent trajectories in the phase space is computed for each portrait, in accordance with procedural step 325, where the rate of divergence reflects the level of chaoticity associated with the corresponding signal. In addition, an average rate and standard deviation of divergence is periodically derived for each signal, in accordance with step 330, wherein each average rate of divergence value is based on numerous rate of divergence values within a "sliding" time window. The average rate of divergence values associated with each signal are then compared to the average rate of divergence values associated with each of the other signals, as shown in procedural step 335, using a statistical measure (e.g. T-index).

When the procedure illustrated in FIG. 3 is first employed, for example, in conjunction with a new patient, there will be an initialization period. During this initialization period, in accordance with the "YES" path out of decision step 340, signals generated by the brain are acquired, processed and compared in accordance with procedural steps 305 through 335, before, during and immediately following at least one, if not several seizures. Then, following each seizure, as indicated by the "YES" path out of decision step 345, a number of "critical" channel pairs may be identified, in accordance with procedural step 360, based on the average rate of divergence comparison accomplished, in accordance with procedural step 335, for each and every pair of signals. For the purpose of the present invention, a critical channel pair is, in general, defined as a pair of signals that shows a relatively high degree of correlation (e.g., statistically significant low T-index values between their corresponding average rates of divergence), well before seizure onset.

Once the list of critical channel pairs has been sufficiently refined (e.g., when no new pair of signals appears in the selection process after the first typical seizures are analyzed), the initialization period is terminated, in accordance with the "NO" path out of decision step 340. Thereafter, the ISW, SSPD and TISP functions may be activated and the average rate of divergence comparisons associated with the critical channel pairs are used to generate an ISW, SSPD and/or TISP in a timely manner, in accordance with steps 350 and 355.

It is important to note that procedural step 360 is accomplished during and after the initialization period. This step is a very important part of the present invention. It is based on observations that seizures are resetting mechanisms of the brain's spatio-temporal entrainment with the epileptogenic focus, which is the precursor of an impending seizure. See J. C. Sackellares et al. "Epileptic Seizures as Neural Resetting Mechanisms," Epilepsia, vol. 38, p. 189, 1997. The reason it is important to continuously update the list of critical channel pairs, from one seizure to the next, even after the initialization period has ended (i.e., after the activation of the ISW, SSPD and TISP features) is that the brain does not necessarily reset itself completely after each seizure and, as a result, the spatio-temporal characteristics associated with any channel pair may be altered, a pair of signals previously identified as being a critical channel pair may have to be removed from the critical channel pair list, while a pair of signals that was not previously identified as being a critical channel pair may have to be added to the list of critical channel pairs to be used for a next ISW, SSPD or TISP.

As previously stated, the procedure depicted in FIG. 3 is intended to illustrate a general procedure in accordance with exemplary embodiments of the present invention. The specific techniques, and alternatives thereto, used to implement each of the various procedural steps will now be described in greater detail herein below.

As illustrated in FIG. 3, procedural step 305 involves the acquisition of electrical or electromagnetic signals generated by the brain. In accordance with a preferred embodiment of the present invention, electroencephalography is typically employed to record electrical potentials using electrodes, where two electrodes correspond to a separate channel, and where the recordings are made using differential amplifiers. In referential recordings, one of the electrodes is common to all channels. The electrode pairs are strategically placed so that the signal associated with each channel is derived from a particular anatomical site in the brain. Electrode placement may include, for example, surface locations, where the electrodes are placed directly on a patient's scalp. Alternatively, subdural electrode arrays and/or depth electrodes are sometimes employed when it is necessary to obtain signals from intracranial locations. However, one skilled in the art will appreciate that the specific placement of the electrodes will depend upon the patient, as well as the application for which the signals are being recorded.

Figure 4A:
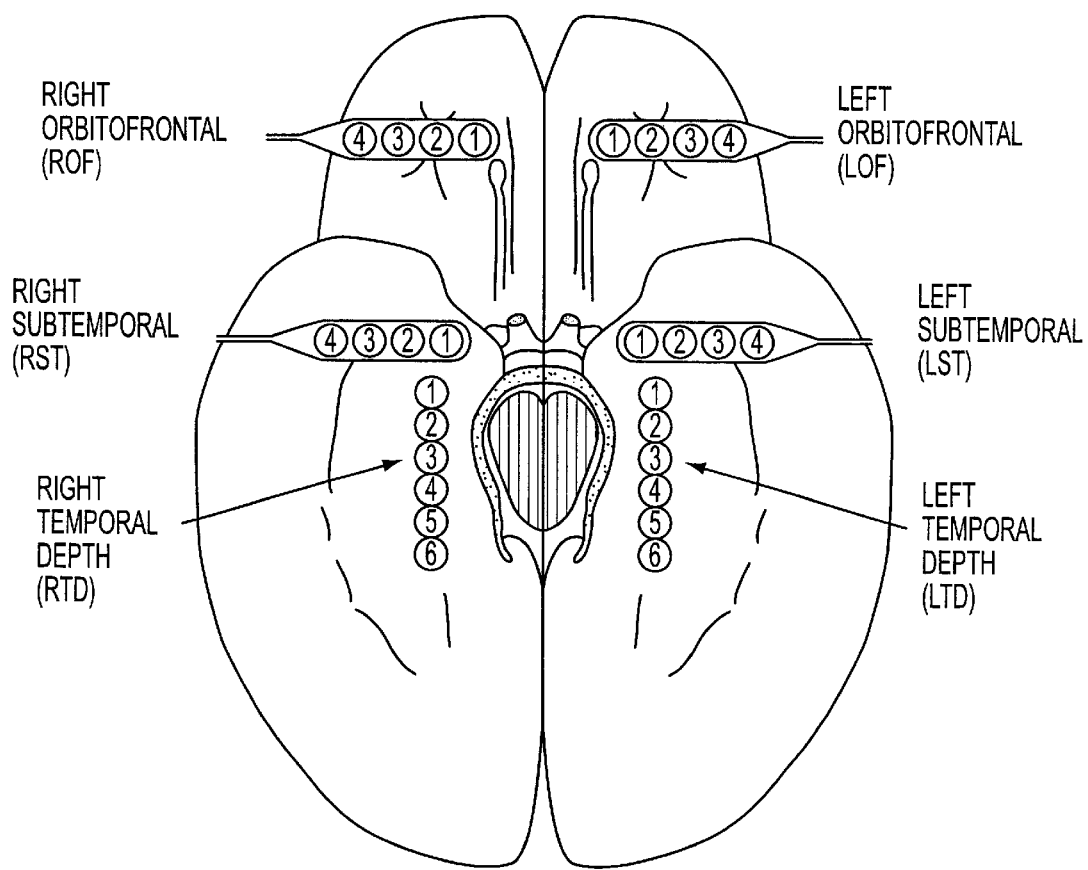
FIGS. 4A and 4B illustrate the placement and use of different electrodes and electrode configurations.
Figure 4B:
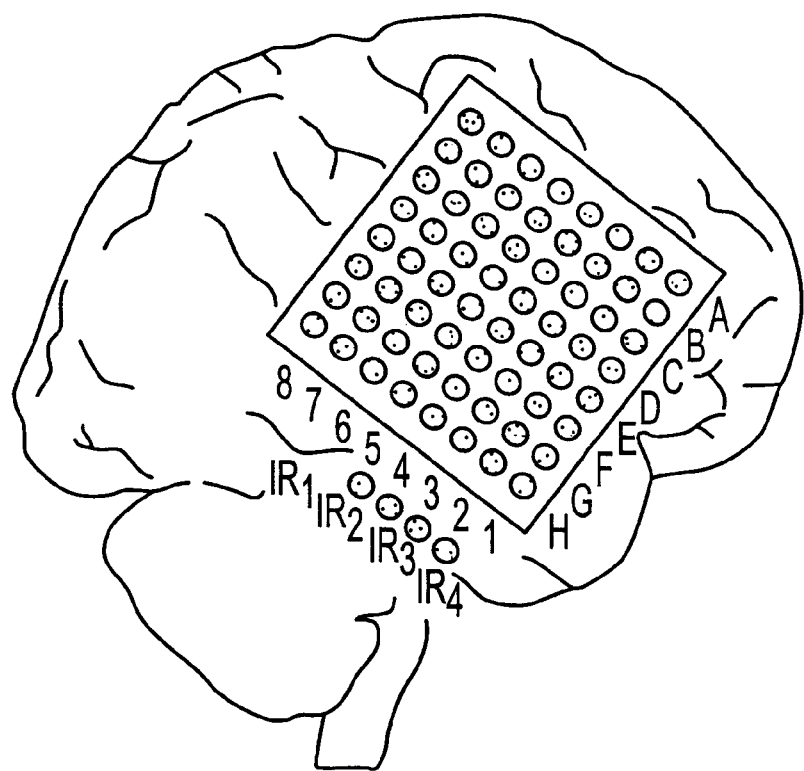

FIG. 4A provides a view from the inferior aspect of the brain and exemplary locations for a number of depth and subdural electrodes. As shown, the electrodes include six right temporal depth (RTD) electrodes and six left temporal depth (LTD) electrodes located along the anterior-posterior plane in the hippocampi. FIG. 4A also includes four right orbitofrontal (ROF), four left orbitofrontal (LOF), four right subtemporal (RST) and four left subtemporal (LST) subdural electrodes located beneath the orbitofrontal and subtemporal cortical surfaces. FIG. 4B illustrates the placement of and use of a subdural electrode array as well as a strip of electrodes on the inferior right temporal lobe.

In accordance with an alternative embodiment of the present invention, magneto-electroencephalography (MEG) may be employed to record the magnetic fields produced by the brain. With MEG, an array of sensors called superconducting quantum interference devices (SQUIDs) are used to detect and record the magnetic fields associated with the brain's internal current sources.

In yet another alternative embodiment, micro-electrodes may be implanted into the brain to measure the field potentials associated with one or just a few neurons. It will be understood that the use of micro-electrodes might be advantageous in very select applications, where, for example, it might be necessary to define with a high degree of accuracy the location of the epileptogenic focus prior to a surgical procedure.

The second procedural step 310 illustrated in FIG. 3 involves pre-processing the signals associated with each channel. This pre-processing step includes, for example, signal amplification, filtering and digitization. In a preferred embodiment, filters, including a high pass filter with 0.1 to 1 Hz cutoff and a low pass filter with 70–200 Hz cutoff, are employed. Depending on the application and/or the signal recording environment, other filters may be employed. For instance, if the signals are being recorded in the vicinity of power lines or any electrical fixtures or appliances operating on a 60 Hz cycle, a 60 Hz notch filter or time varying digital filters may be employed. In any event, the preprocessing step 310 results in the generation of a digital time series for each channel.

Procedural step 320 involves generating phase portraits, and in particular, p-dimensional phase space portraits for each channel, where p represents the number of dimensions necessary to properly embed a brain state. In a preferred embodiment of the present invention, the p-dimensional phase space portraits are generated as follows, where p is assumed to be at least seven (7) to capture the dynamic characteristics of the ictal state, which may be present during the preictal state. First, the digital signals associated with each channel are sampled over sequential time segments, referred to herein as epochs. Each epoch may range in duration from approximately 10 seconds to approximately 24 seconds, depending upon signal characteristics such as frequency content, amplitude, dynamic properties (e.g., chaoticity or complexity) and stationarity. Generally, epoch length increases as stationarity increases. In an exemplary embodiment of the present invention, a signal may be sampled approximately 2000 times per epoch, where the epoch is approximately 10 seconds in duration.

The samples associated with each signal, taken during a given epoch, are then used to construct a phase space portrait for the corresponding channel. In a preferred embodiment of the present invention, the phase space portraits are constructed using the "Method of Delays." The Method of Delays is well known in the art and, as stated above, a more detailed discussion of this method with respect to analyzing dynamic, nonlinear systems can be found in the Takens and Whitney publications, as well as Iasemidis et al., "Phase Space Topography of the Electrocorticogram and the Lyapunov Exponent in Partial Seizures", Brain Topogr., vol. 2, pp. 187–201 (1990). In general, a phase space portrait is constructed using the Method of Delays by independently treating each unique sequence of p consecutive sample values, separated by a time delay $\tau$, as a point to be plotted in the p-dimensional phase space. In an exemplary implementation of the present invention, τ equals 4 samples (20 msec).

Figure 5A:
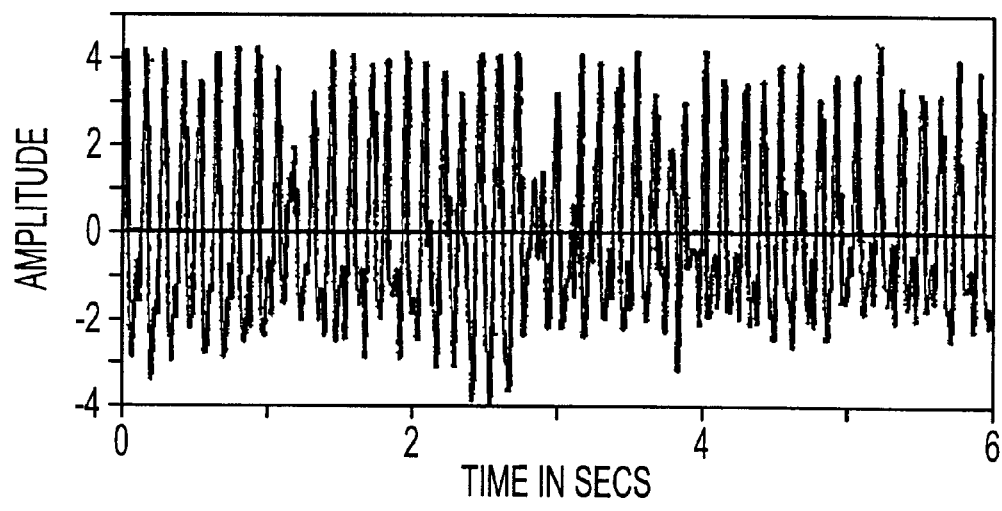
FIGS. 5A and 5B illustrate an EEG signal associated with a representative electrode channel over an epoch and the corresponding phase space portraits containing the attractor reconstructed generated from the EEG signal using the Method of Delays.
Figure 5B:
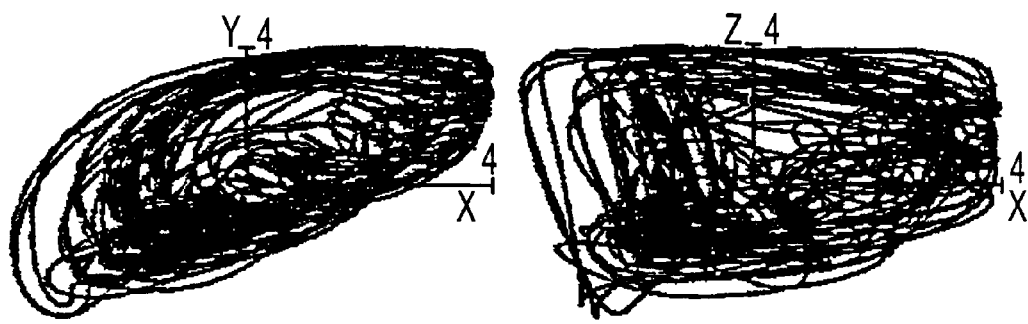

FIG. 5A shows a 6 second epoch associated with an exemplary EEG signal at the onset of a seizure that originated in the left temporal cortex. FIG. 5B illustrates, from different perspectives, the corresponding phase space portrait, projected in three dimensions, for the exemplary EEG signal of FIG. 5A. The object appearing in the phase space portrait of FIG. 5B is called an "attractor".

The attractor represents the region within the phase space in which the states of the system evolve and remain confined thereto until the structure of the system changes.

Procedural step 325 then involves quantifying the chaoticity of the attractor 30 associated with each channel. There are, of course, different techniques that can be used to accomplish this. However, in accordance with a preferred embodiment of the present invention, the chaoticity of each attractor is quantified using Lyapunov exponents, which represents the average rate of divergence (i.e., expansion or contraction) between point pairs of trajectories that are in close proximity to one another in the phase space. In a multidimensional system, the number of possible Lyapunov exponents is equal to the dimension (p) of the reconstructed state space. Therefore, quantifying the system's behavior may involve calculating sequences of one or more Lyapunov exponents. For instance, if the number of dimensions characterizing the state space is seven (7), then seven (7) different Lyapunov exponent sequences may be computed in quantifying the chaoticity of system's behavior. However, to strike a balance between the accuracy of the chaoticity measurements and signal processing efficiency, only the largest Lyapunov exponent (i.e., Lmax) is used in accordance with a preferred embodiment of the present invention. Although one skilled in the art will readily appreciate that it may be desirable to utilize more than one Lyapunov exponent (i.e., Lyapunov exponents in addition to Lmax) in order to optimize sensitivity and specificity of seizure prediction. For example, it may be desirable to use more than the maximum Lyapunov exponent Lmax for cases where it is essential to predict seizure onset time with the highest possible degree of accuracy.

Further, in accordance with a preferred embodiment of the present invention, an Lmax value is ultimately derived for each epoch, thereby resulting in a sequence of Lmax values over time for each channel. This sequence of Lmax values (herein referred to as an Lmax profile) represents the chaoticity of the corresponding channel over time. A more complete explanation regarding the computation and utilization of Lyapunov exponents can be found, for example, in Wolf et al., "Determining Lyapunov Exponents from a Time Series," Physica D, vol. 16, pp. 285–317 (1985) and Eckmann et al., "Lyapunov Exponents from Times Series," Phys. Rev. A, vol. 34, pp. 4971–4972 (1986). In the Iasemidis et al., publication entitled "Phase Space Topography of the Electrocorticogram and the Lyapunov Exponent in Partial Seizures", a method for computing and utilizing short-term Lyapunov exponents (i.e., STLmax) is described, wherein the method takes into account the nonstationarity of the EEG data, a feature of paramount importance for the accurate estimation of Lmax from EEG in epileptic patients. The reason this feature is so important is the existence of excessive transients (e.g., epileptic spikes, fast or slow wave transients etc.) in the EEG from such patients.

Figure 6:
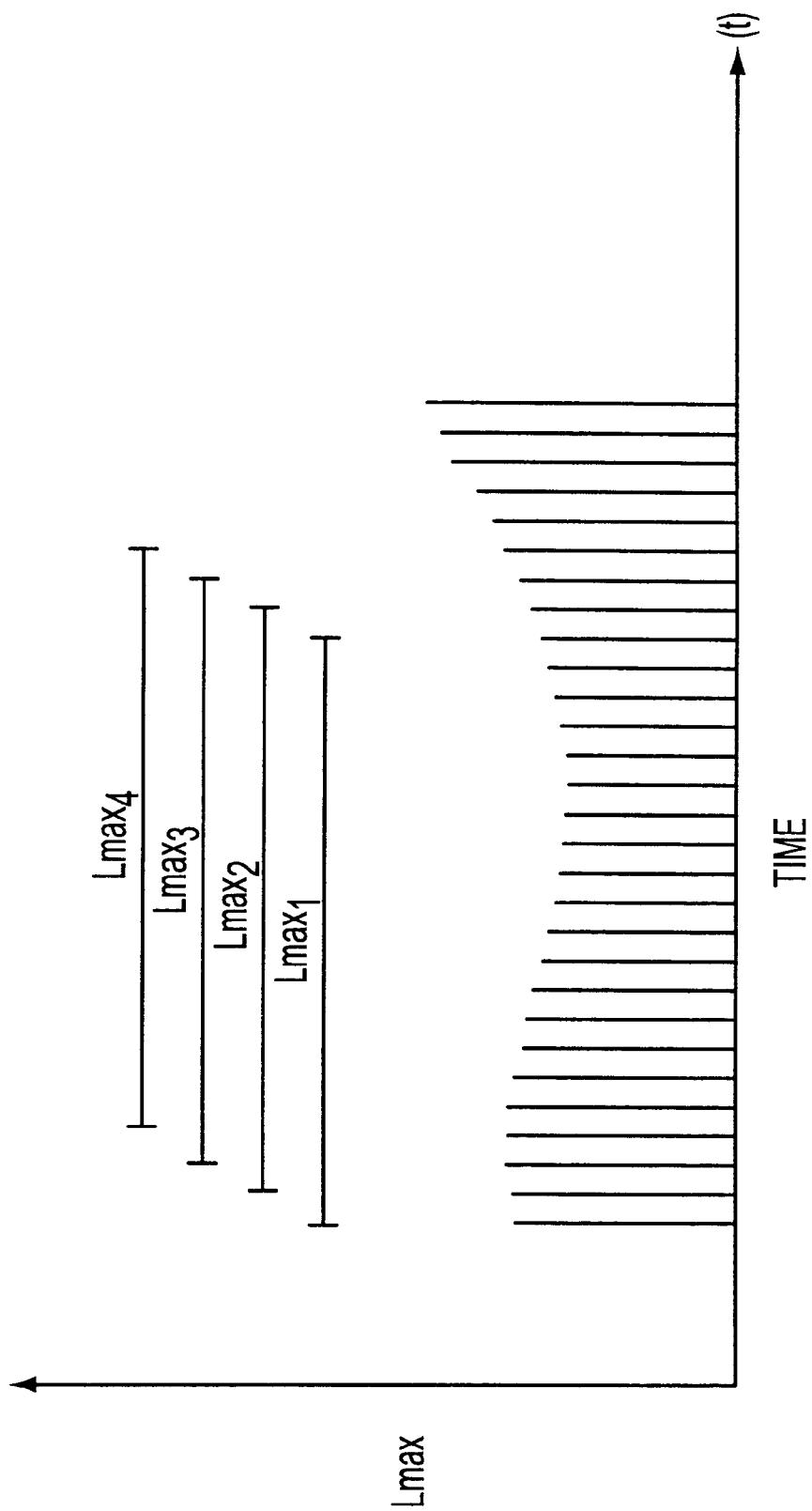
FIG. 6 illustrates a procedure for calculating Lmax profiles for sequential epochs.

Procedural steps 330 and 335 involve evaluating the entrainment of the Lmax profiles associated with each channel pair. First, in order to estimate the statistics of the dynamical measures involved, a sequence of average Lmax values and standard deviation values for Lmax are derived for each channel over time, in accordance with procedural step 330. In a preferred embodiment, each average Lmax value is derived based on a number of consecutive Lmax values that fall within a "sliding" time window, that may include several epochs, as illustrated in FIG. 6. The length of time associated with the time windows may, of course, vary. However, in accordance with a preferred embodiment of the present invention, the length of time associated with the "sliding" time windows is approximately 5 minutes (i.e., a span of approximately 30 epochs). Thus, procedural step 330 results in a sequence of average Lmax values over time for each channel.

In general, step 335 involves comparing the Lmax profile associated with each channel to the Lmax profile associated with each of the other channels, in order to determine whether the corresponding pair of signals show signs of entrainment. For the purpose of the present invention, the term "entrain" refers to a correlation or convergence in amplitude and/or phase between two signals that make up a channel pair. Although any number of statistical methods may be employed to quantify the degree of correlation between a pair of signals, a T-test is employed for this purpose in accordance with a preferred embodiment of the present invention.

By applying the T-test, a T-index is derived for each of a number of overlapping or non-overlapping "sliding" time windows for each channel pair, wherein the duration of a time window may vary from approximately 1 minute to 20 minutes. As already mentioned, in a preferred embodiment of the present invention, the duration of these "sliding" time windows is approximately 5 minutes. Optimally, the length of time associated with these time windows must capture, with sufficient resolution, and a minimum number of computations, the dynamic spatio-temporal transitions during the preictal stage. Since the preictal transitions are characterized by the progressive entrainment of Lmax profile pairs (i.e., the Lmax profiles associated with each channel pair), it is the rate of entrainment between Lmax profile pairs and the level of statistical significance that determines the optimum length of these time windows.

Figure 7:
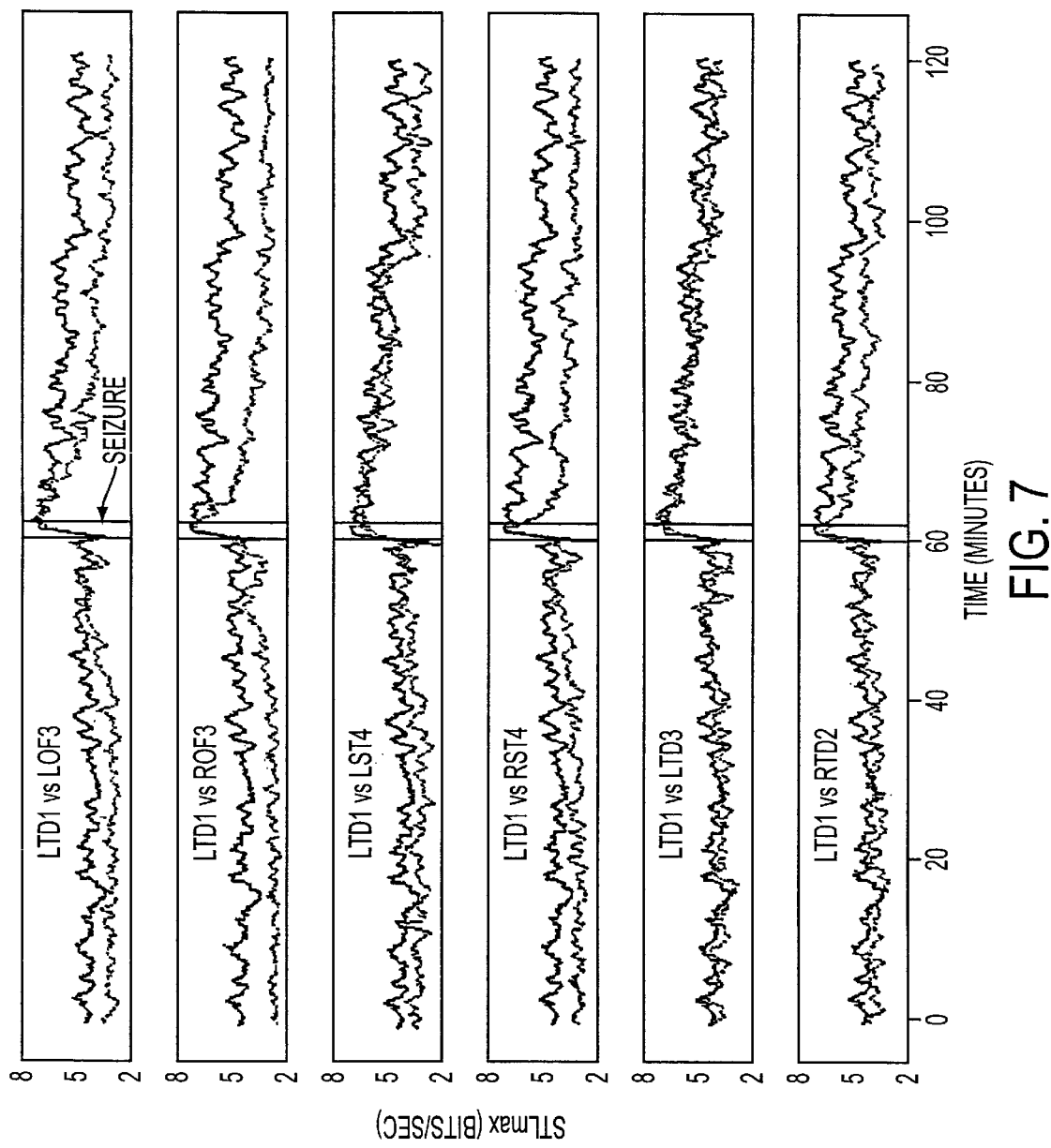
FIG. 7 illustrates the Lmax profiles associated with each of a representative number of channel pairs.

FIG. 7 illustrates a comparison between the Lmax profiles associated with each of a representative number of channel pairs. More particularly, FIG. 7 shows a comparison between the Lmax profile corresponding to a signal associated with a left temporal depth electrode LTD1 and the Lmax profiles associated with six other representative electrode sites. The six other representative electrode sites are a left orbitofrontal electrode LOF3, a right orbitofrontal electrode ROF3, a left subtemporal electrode LST4, a right subtemporal electrode RST4, a left temporal depth electrode LTD3 and a right temporal depth electrode RTD2. Although FIG. 7 only shows Lmax profile comparisons for six representative channel pairs, in a preferred embodiment of the present invention, procedural step 335 would typically involve Lmax profile comparisons associated with more than six channel pairs. For example, if signals are being recorded at 20 different electrode sites, procedural step 335 would typically involve 190 Lmax profile comparisons, as there are 190 different channel pairs.

Figure 8:
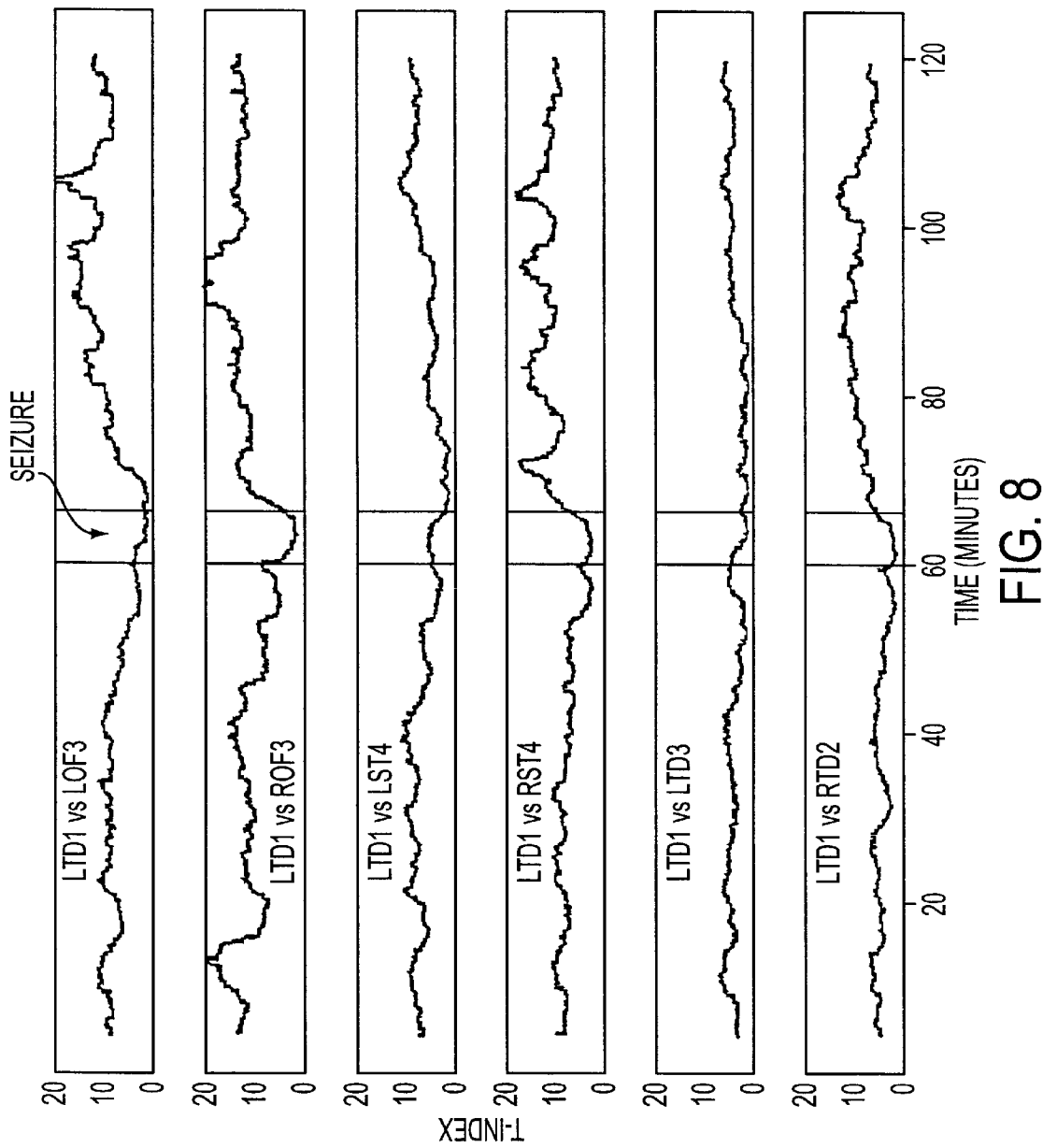
FIG. 8 illustrates a procedure for comparing Lmax profiles (e.g., estimations of T-index profiles) for the representative number of channel pairs shown in FIG. 7.

FIG. 8 illustrates the T-index profiles associated with the six channel pairs illustrated in FIG. 7. From the T-index profiles illustrated in FIG. 8, it is evident that the Lmax profiles associated with each of the six channel pairs all progressively become entrained during the preictal stage, while each channel pair becomes progressively disentrained during the postictal stage. However, the rate and degree to which the Lmax profiles become entrained and disentrained vary. In the example illustrated in FIG. 8, the channel pair associated with the electrode LTD1 and the electrode LTD3 demonstrates a relatively high level of entrainment (i.e., relatively low T-index values), more so than the other five signal pairs. The channel pair associated with the electrode LTD1 and the electrode RTD2 also shows a relatively high level of entrainment, particularly during the preictal stage. Although FIG. 8 only shows T-index values 60 minutes prior to and 60 minutes following seizure onset, the preictal period typically begins approximately 15 minutes to as much as 2 hours prior to seizure onset. However, it is extremely important to note that signs of entrainment, such as reduced T-index values without statistical significance between certain signals, particularly those associated with critical channel pairs, may be evident long before seizure onset. In fact, it is possible that critical channel pairs will exhibit signs of an impending seizure days before an actual seizure.

Further in accordance with a preferred embodiment of the present invention, procedural steps 340, 345 and 360 involve the establishment of an initialization period, and thereafter, the update and/or maintenance of a library or list of critical channel pairs. For the purpose of the present invention, a critical channel pair is defined as a pair of signals which together exhibit properties (e.g., entrainment) indicative of an impending seizure well in advance of other channel pairs, for example, the pair of signals associated with electrodes LTD1 and LTD3 illustrated in FIG. 7 and FIG. 8. Identifying certain channel pairs as critical channel pairs is, as illustrated in the flowchart of FIG. 3, a post-seizure event that is based on the Lmax profile comparison data (i.e., the T index profiles) derived for each channel pair before, during and after a seizure. It is of particular importance to note that creating and maintaining the critical channel pair library is an iterative or adaptive process, in that, after each seizure, new channel pairs may be added to the critical channel pair library, while other channel pairs previously identified as being critical channel pairs, may be removed from the library. Typically, one to six seizures are required to create and refine the critical channel pair library during the initialization period.

Refinement of the critical channel pair library is very important because, after the initialization period has ended, it is the behavior of the critical channel pairs that is analyzed in real-time in support of the ISW, SSPD and TISP features, in accordance with procedural step 350. Refinement of the critical channel pair library tends to reduce false positive detections, predictions and warnings.

The specific techniques employed to generate an ISW, SSPD and/or TISP, in accordance with procedural step 355, will now be described in greater detail herein below. The first of these features to be described is the early ISW feature. In general, an ISW is triggered when one or more of the critical channel pairs become entrained for a statistically significant period of time. More specifically, an ISW is generated when the average T index value associated with one or more critical channel pairs falls below a statistically significant threshold value for a statistically significant period of time. In a preferred embodiment, the threshold is set at a value of $T<T_c$, wherein $T_c = 2.09$, such that the use of 5-minute sliding windows results in a statistical level of significance of a type I error of less than 5 percent (i.e., <0.05). Further in accordance with a preferred embodiment, the statistically significant period of time during which the average T index value must remain below 2.09 in order to trigger an ISW is typically set somewhere between 15 minutes and 1.5 hours. For example, a T index value less than 2.09 for a period of time equal to 15 minutes equates to a 99 percent confidence level that the issuance of an ISW is, in fact, a valid warning. Of course, it will be understood that the threshold value and the duration which the average T index must remain below that threshold may be adjusted to increase or decrease ISW sensitivity and reduce the incidence of false warnings (i.e., false positives) for any given patient, or reduce the incidence of failed warnings (i.e., false negatives).

The ISW may be implemented in any number of ways. For example, the ISW may involve audible warnings or visual warnings or a combination of both visual and audible warnings. In fact, the ISW may involve nothing more than the setting or resetting of an internal software variable or flag, wherein the setting or resetting of the variable or flag triggers a dependent event, such as the automatic delivery of anti-seizure medication. Accordingly, the specific implementation of the ISW will depend on the application for which the present invention is being employed.

Figure 9:
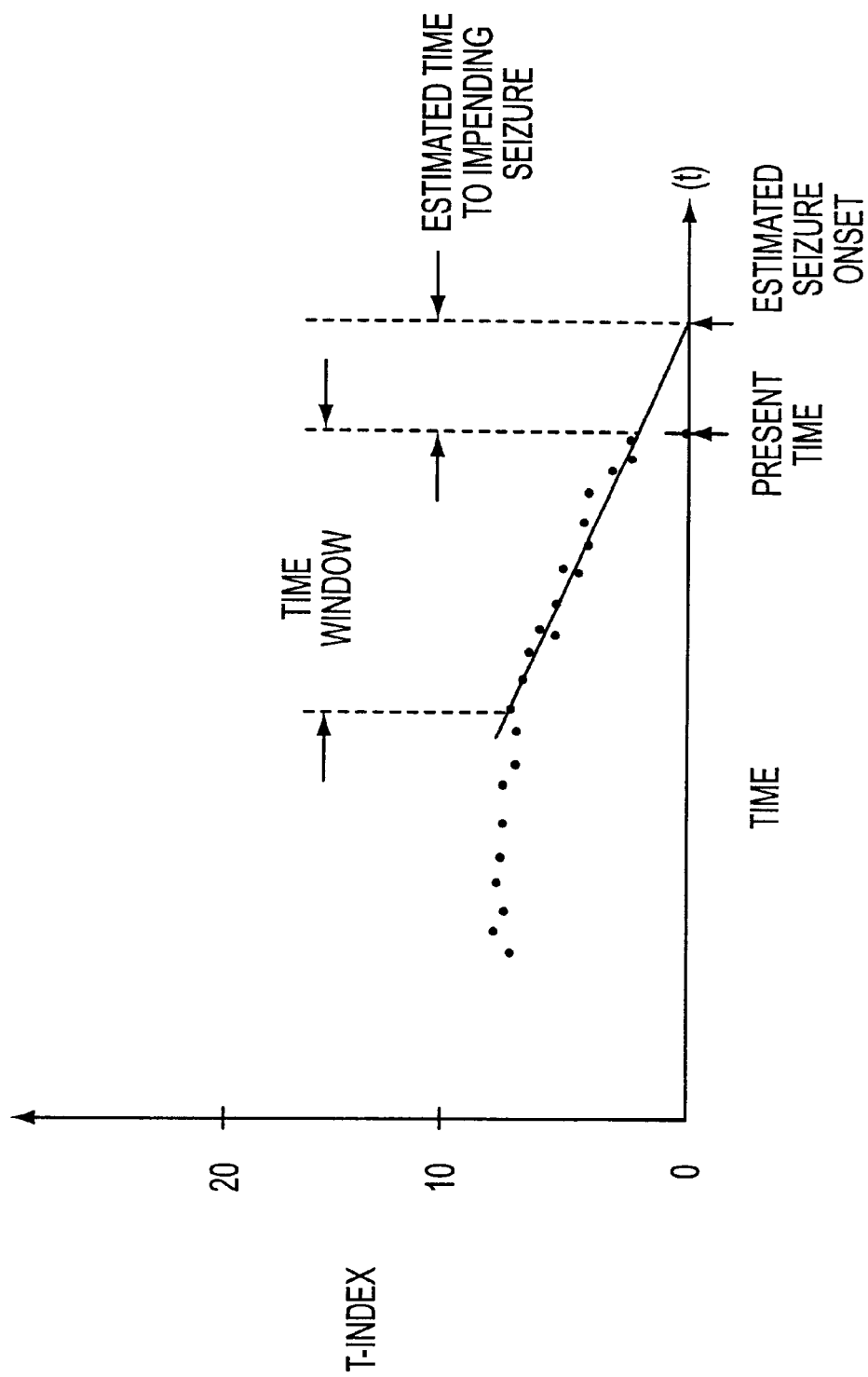
FIG. 9 illustrates the Time to Impending Seizure (TIS) feature in accordance with exemplary embodiments of the present invention.

The next feature to be described is the TIS feature. Once an impending seizure warning has been generated, the rate of entrainment, that is, the rate at which the Lmax profiles associated with a critical channel pair continue to converge, can be used to periodically estimate the amount of time before seizure onset. In accordance with a preferred embodiment of the present invention, this is accomplished by continuously deriving, for each of one or more critical channel pairs, the "slope" of the T-index profile over a "sliding" time window, as illustrated in FIG. 9. The point at which the slope intercepts the time (t) axis represents an estimated seizure onset time. Therefore, the difference between the present time and the estimated seizure onset time, along the time (t) axis, represents the TISP. The length of the "sliding" time window may, once again, vary. Initially, it may be set to a relatively small time interval (e.g., 15 minutes). Thereafter, it may be adaptively optimized for each individual patient.

The last of the three features is the SSPD feature. Over a period of several hours, if not several days, prior to a seizure, or a first of a series of seizures, there is generally a gradual spatial entrainment among critical cortical sites. This gradual entrainment is thus exploited by the present invention to provide the SSPD feature. More specifically, the SSPD feature is, in accordance with a preferred embodiment of the present invention, implemented in much the same way as the ISW feature, that is, by generating a T-index profile for each of one or more critical channel pairs, and by observing those T-index profiles. However, the T-index profiles are typically generated and observed over a period of numerous hours or days, rather than a period of minutes.

Figure 10A:
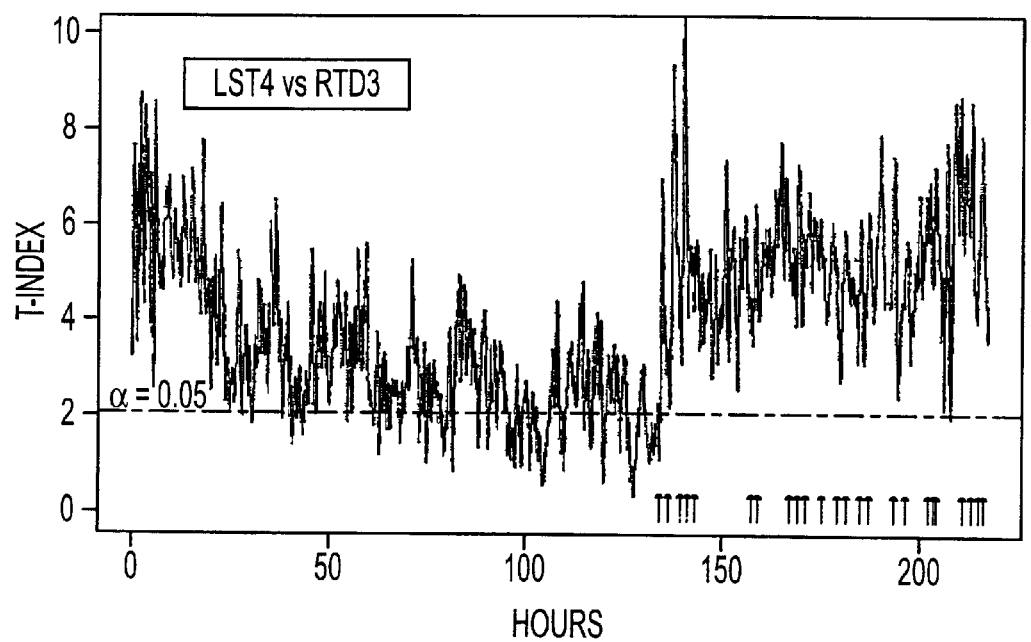
FIGS. 10A and 10B illustrate the T-index profiles associated with two electrode pairs calculated over a 10-day period.
Figure 10B:
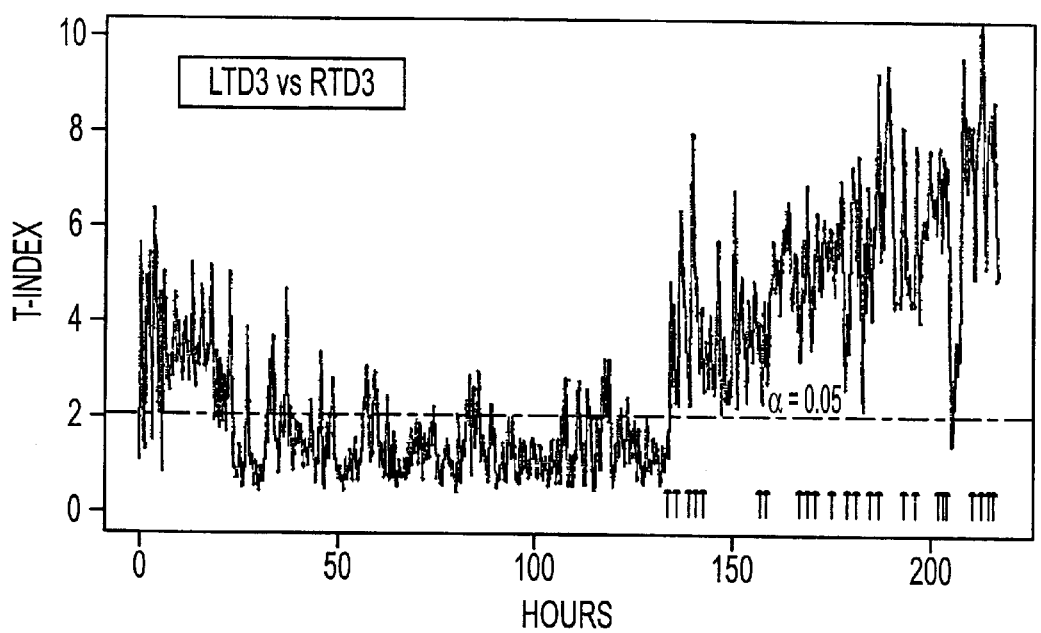

FIGS. 10A and 10B illustrate the T-index profiles associated with two electrode pairs calculated over a 10-day period. The patient was seizure-free during the first 135 hours of the recording. However, over the subsequent 90 hours, the patient experienced 24 seizures, as indicated by the 24 arrows located along the time (hours) axis.

FIG. 10A shows the T-index profile associated with a focal electrode RTD3 and a contralateral subtemporal electrode LST4. For this electrode pair, dynamic entrainment occurred gradually, where the value of the T-indices fell below critical values only after the third day of recording. At the onset of seizures, resetting of entrainment occurs.

Referring now to FIG. 10B, it is of particular interest that the T-index profile associated with the bilateral hippocampal electrodes LTD3 and RTD3 falls below the statistically significant threshold value $T_c$, approximately one (1) day into the recording, thus indicating that the signals associated with the electrode pair are entrained approximately four (4) days prior to the first seizure. Moreover, the signals associated with this pair of electrodes remain mostly entrained until the first seizure, after which, the T-index profile values begin to reset progressively. Again, the present invention exploits this behavior in order to provide the above-described SSPD feature. It should be noted that due to the time resolution (i.e., minutes) used for FIGS. 10A and 10B, resetting after each individual seizure cannot be visualized in these figures.

As described above, the seizure warning and prediction technique illustrated in FIG. 3 relies on a comparison between two Lmax profiles for each of a number of channel pairs, where each Lmax profile is derived from a signal measured at a corresponding electrode site. More importantly, the seizure warning and prediction technique described above relies on a comparison of Lmax profiles for each of a number of critical channel pairs, where a critical channel pair has been defined as a pair of channels whose corresponding signals exhibit a relatively high degree of correlation with respect to one another, well before seizure onset. However, in some instances, seizure warning and seizure prediction may be improved by comparing the Lmax profiles associated with groups of three (3) or more channels (i.e., electrode site triplets, quadruplets, etc . . .). In such instances, it may not be appropriate to employ a T-index statistic. For example, an F-index statistic (i.e., ANOVA statistic) may be employed instead of a T-index statistic, if Lmax profiles associated three or more channels are being compared. Yet another alternative is to employ neural network technology and pattern recognition techniques to analyze the level of entrainment between groups of two, three or more Lmax profiles.

In general, the physical implementation of the technique illustrated in FIG. 3 involves a combination of software, using standard programming techniques, hardware and/or firmware. Once again, however, the specific physical implementation will depend, to a large extent, on the application as illustrated herein below.

Figure 11:
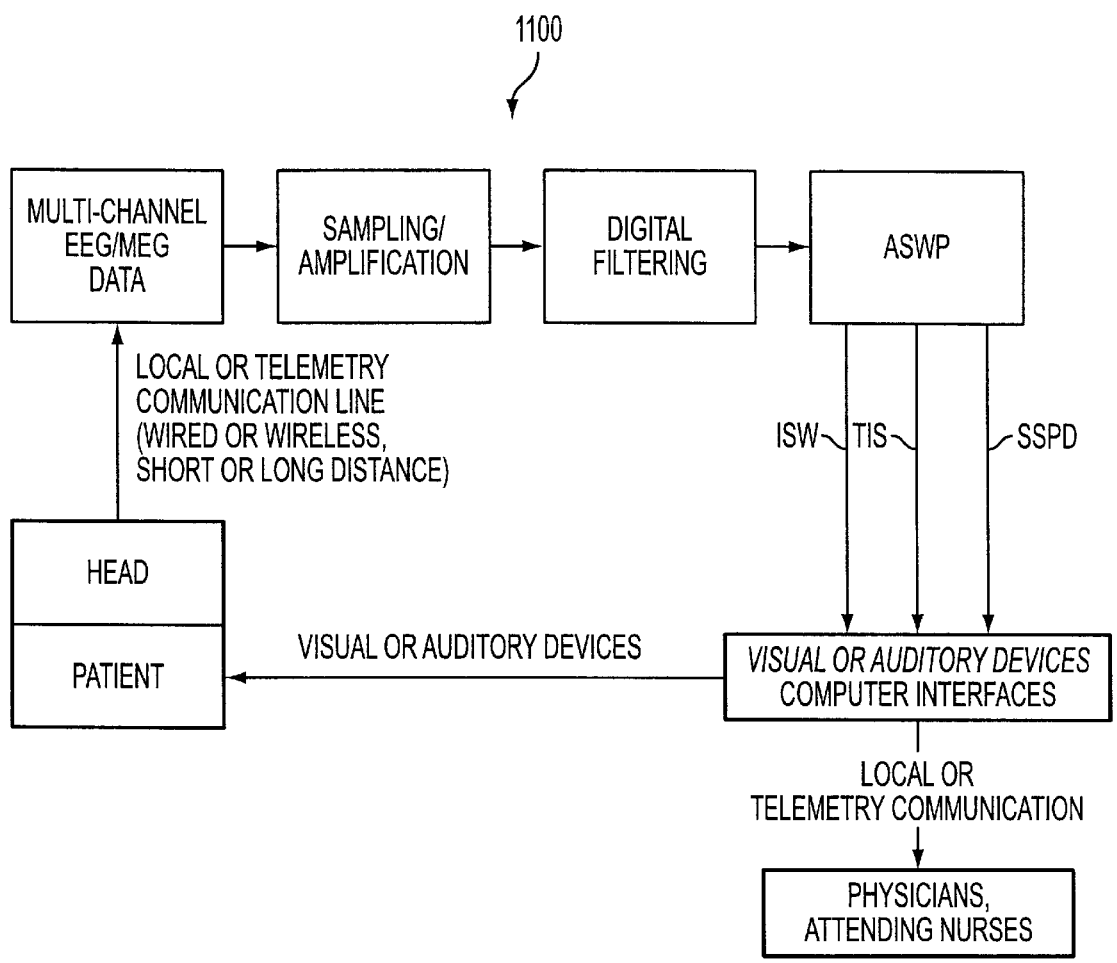
FIG. 11 illustrates an on-line system that incorporates the Impending Seizure Warning, Time to Impending Seizure and Seizure Susceptibility Determination features of the present invention.

In accordance with one alternative physical embodiment of the present invention, FIG. 11 illustrates an on-line system 1100 that incorporates the various features of the present invention, as described above. The on-line system 1100 is primarily intended for use in any number of in-patient applications including diagnostic applications, as well as applications relating to patient treatment. For example, the on-line system 1100 may be used to collect and process EEG or MEG signals for subsequent clinical interpretation (e.g., to analyze and determine seizure propagation patterns). The on-line system 1100 might also be used to alert hospital or clinic staff members of an impending seizure, via a local or telemetry link, so that staff members have adequate time to prevent patient injury or provide timely medical intervention to prevent the seizure itself; to observe the seizure; or to prepare for and administer other procedures that must be accomplished during the seizure, such as the administration of radiolabelled ligands or other substances required to obtain ictal SPECT, ictal FMRI, or ictal PET images for pre-surgical diagnostic purposes.

In addition to surgical excision of the epileptogenic focus, current methods for controlling epileptic seizures include pharmacological (i.e., antiepileptic drug) therapy. The currently accepted pharmacological approach is to prescribe fixed doses of one or more antiepileptic drugs (e.g. phenytoin, phenobarbital, carbamazepine, divalproex sodium, etc.) to be taken chronically at fixed time intervals. The objective is to achieve a steady-state concentration in the brain that is high enough to provide optimal seizure control, but low enough to reduce the risk of side-effects.

Figure 12:
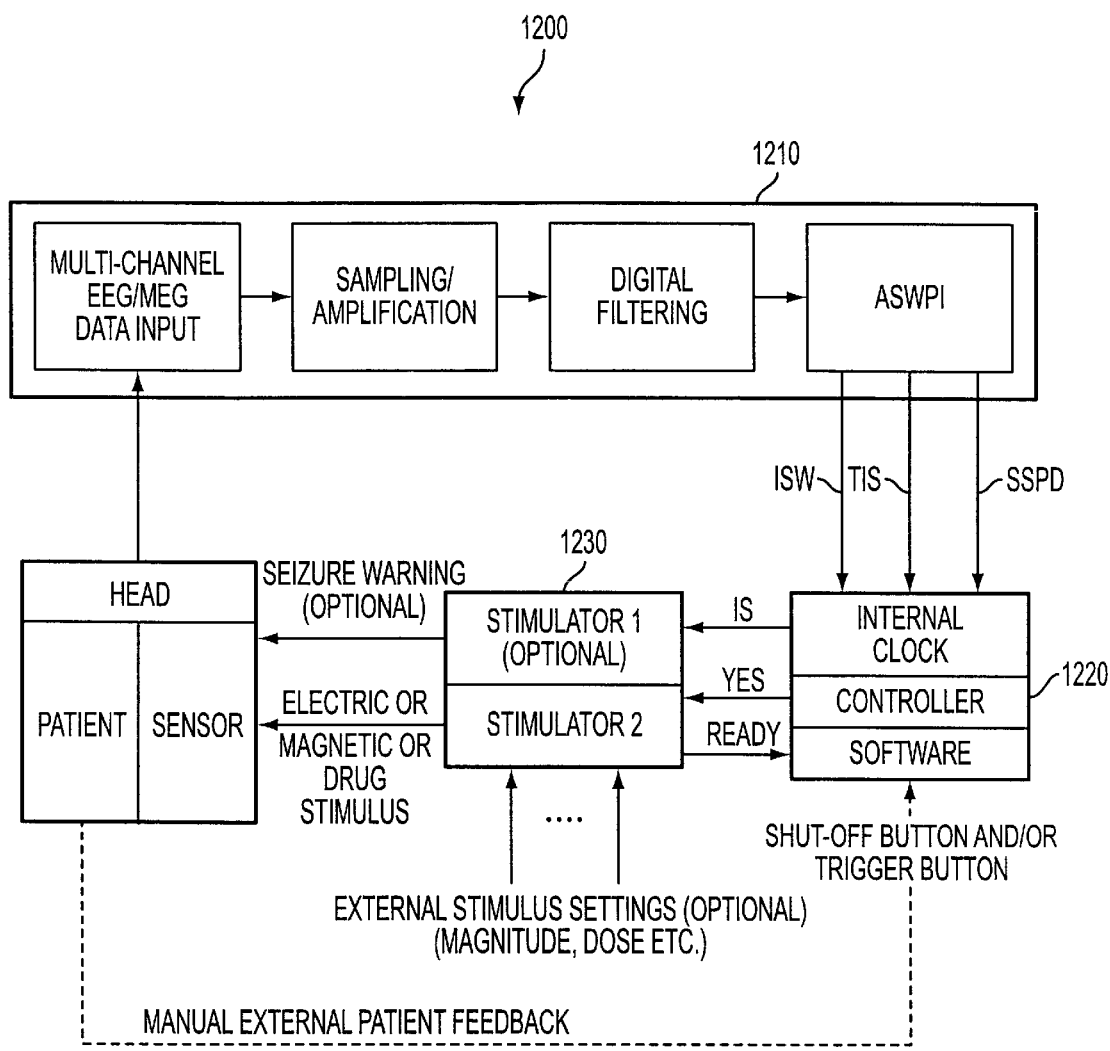
FIG. 12 illustrates a therapeutic intervention system that incorporates an indwelling device capable of providing Impending Seizure Warning, Time to Impending Seizure and Seizure Susceptibility Determination in accordance with the present invention.

Given the currently accepted pharmacological approach described above, FIG. 12 illustrates another alternative physical embodiment of the present invention. More particularly, FIG. 12 illustrates a pharmacological antiepileptic seizure system that includes an indwelling device, such as a real-time digital signal processing chip 1210, that contains, among other things, an algorithm that is capable of providing seizure warning and prediction (ASWP), in accordance with the present invention, as described above. As illustrated in FIG. 12, the ISW, TIS, and SSPD signals generated by the indwelling device 1210 are forwarded to a controller 1220. The controller 1220 can then trigger the release of a compound, such as a small dose of an anticonvulsant drug, into the blood stream of the patient, from a stimulator 1230 which contains or is connected to an indwelling reservoir 1230. The objective, of course, is to release a small quantity of anticonvulsant drug during the preictal transition stage to abort an impending seizure.

FIG. 12 also illustrates that the therapeutic intervention system 1200 may, in addition to delivering anticonvulsant drug therapy, deliver electric or magnetic stimulation, for example, through a vagal nerve stimulator. Vagal nerve stimulators are currently used to deliver electrical impulses to the vagus nerve in the patient's neck at externally specified intervals, in an arbitrary fashion, with a specified duration and intensity. In contrast, the present invention, in accordance with the exemplary embodiment illustrated in FIG. 12, delivers an electrical impulse to the vagus nerve in the neck of specified duration and intensity, but the impulse is delivered only during the preictal transition state. To accomplish this objective, the indwelling device 1210 detects the preictal transition state based on dynamical analysis of ongoing brain electrical activity, as described in detail above. When an impending seizure is detected, the indwelling vagal nerve stimulator is triggered and an electrical pulse is delivered to the vagus nerve in the neck. It will be readily apparent, however, to those skilled in the art that devices other than vagal nerve stimulators may be used in conjunction with the present invention.

The present invention has been described with reference to a number of exemplary embodiments. However, it will be readily apparent to those skilled in the art that it is possible to embody the invention in specific forms other than those described above without departing from the spirit of the invention. In fact, it will be readily apparent that the present invention may be employed for non-medical, non-linear, multidimensional processes characterized by sudden phase transitions. Accordingly, the various embodiments described above are illustrative, and they should not be considered restrictive in any way. The scope of the invention is given by the appended claims, rather than the preceding description, and all variations and equivalents thereof which fall within the range of the claims are intended to be embraced therein.

What is claimed is:

1. A method of analyzing a multidimensional system comprising the steps of:

measuring each of a plurality of signals generated by said multidimensional system, wherein each of the plurality of signals represents a response associated with a corresponding spatial location within said multidimensional system;

generating a phase space representation for each of the plurality of signals;

deriving a signal profile for each of the plurality of signals, wherein each signal profile represents a level of chaoticity for each corresponding signal over time;

comparing each of the signal profiles;

selecting one or more groups of signals based on the comparison between their corresponding signal profiles; and characterizing the state dynamics of the multidimensional system as a function of the signal profile comparisons associated with the selected one or more signal groups.

2. The method of claim 1, wherein said multidimensional system is the brain.

3. The method of claim 2, wherein said step of characterizing the state of the multidimensional system as a function of the signal profile comparisons associated with the selected one or more signal groups comprises the step of:

determining whether the brain is likely to experience a seizure.

4. The method of claim 3 further comprising the step of: determining a time to impending seizure.

5. The method of claim 3 further comprising the step of: deriving a time to impending seizure.

6. The method of claim 1 further comprising the step of: issuing a warning of a state transition based on the characterized state dynamics of the multi-dimensional system.

7. The method of claim 1 further comprising the step of: predicting a time of occurrence of a state transition based on the characterized state dynamics of the multi-dimensional system.

8. The method of claim 1, wherein said step of deriving a signal profile for each of the plurality of signals comprises the step of:

determining a plurality of Lyapunov exponent values over time for each of the plurality of signals.

9. The method of claim 1 further comprising the step of: deriving additional signal profiles for each of the plurality of signals, wherein each of the signal profiles associated with a corresponding signal represents a level of chaoticity for that corresponding signal based on a different Lyapanov exponent.

10. The method of claim 9, wherein one of the signal profiles associated with each signal represents a level of chaoticity for the corresponding signal based on a maximum Lyapunov exponent.

11. The method of claim 9, wherein the number of signal profiles derived for a corresponding signal equals the number of dimensions of said multidimensional system.

12. The method of claim 1 wherein said step of comparing each of the signal profiles comprises the step of:

determining a degree of correlation between the signal profiles.

13. The method of claim 12, wherein said step of determining a degree of correlation between the signal profiles comprises the step of:

determining a level of entrainment between the signal profiles.

14. The method of claim 13, wherein said step of determining the level of entrainment between the signal profiles comprises the step of:

applying a T-index statistic to quantify the level of entrainment between the signal profiles.

15. The method of claim 13, wherein said step of determining the level of entrainment between the signal profiles comprises the step of:

applying an F-index statistic to quantify the level of entrainment between the signal profiles.

16. The method of claim 13, wherein said step of determining the level of entrainment between the signal profiles comprises the step of:

employing neural network to quantify the level of entrainment between the signal profiles.

17. The method of claim 13, wherein said step of determining the level of entrainment between the signal profiles comprises the step of:

employing pattern recognition techniques to quantify the level of entrainment between the signal profiles.

18. The method of claim 13, wherein said step of determining a level of entrainment between the signal profiles comprises the step of:

determining a level of phase entrainment between the signal profiles.

19. The method of claim 13, wherein said step of determining a level of entrainment between the signal profiles comprises the step of:

determining a level of entrainment between the signal profiles using higher order derivatives of the signal profiles.

20. A method for providing seizure warnings comprising the steps of:

acquiring a time series signal from each of a plurality of locations about the brain, wherein each signal and its corresponding location constitute a corresponding channel;

for each channel, generating a spatio-temporal response based on the corresponding time series signal;

quantifying a sequence of chaoticity values for each channel based on the corresponding spatio-temporal response, wherein each sequence of chaoticity values constitutes a chaoticity profile;

comparing, over time, the chaoticity profiles associated with each of a number of channel pairs;

evaluating, over time, levels of entrainment between the chaoticity profiles associated with each of the channel pairs;

determining whether the levels of entrainment associated with one or more of the channel pairs are statistically significant; and generating a seizure warning if it is determined that the levels of entrainment associated with one or more of the channel pairs are statistically significant.

21. The method of claim 20 further comprising the step of:

selecting a number of critical channel pairs during an initialization period, wherein a critical channel pair is identified as a pair of channels whose corresponding chaoticity profiles exhibit a relatively high level of entrainment prior to a seizure; and wherein each of said number of channel pairs is a critical channel pair.

22. The method of claim 21 further comprising the steps of:

refining the selection of critical channel pairs after a seizure; and using the refined selection of critical channel pairs in generating a seizure warning for a next seizure.

23. The method of claim 20, wherein said step of acquiring a time series signal from each of the plurality of locations about the brain comprises the step of:

measuring electrical signals from each of the locations about the brain using electroencephalography.

24. The method of claim 20, wherein said step of acquiring a time series signal from each of the plurality of locations about the brain comprises the step of:
   measuring electromagnetic signals from each of the locations about the brain using magneto-electroencephalography.

25. The method of claim 20 further comprising the step of:
   digitizing each of the acquired time series signals.

26. The method of claim 20, wherein said step of generating a spatio-temporal response based on the corresponding time series signal comprises the step of:
   generating a p-dimensional phase space portrait from each time series signal using the Method of Delays.

27. The method of claim 20, wherein said step of quantifying a sequence of chaoticity values for each channel based on the corresponding spatio-temporal response, wherein each sequence of chaoticity values constitutes a chaoticity profile, comprises the step of:
   computing a sequence of Lyapunov exponents; and
   generating a sequence of average Lyapunov exponents by averaging the Lyapunov exponents over "sliding time windows".

28. The method of claim 27 further comprising the step of:
   quantifying a plurality of chaoticity value sequences, each chaoticity value sequence constituting a distinct chaoticity profile, wherein a chaoticity value sequence is produced for each channel based on a corresponding spatio-temporal response, and wherein each of the chaoticity profiles associated with each channel is based on a different Lyapunov exponent.

29. The method of claim 28, wherein one chaoticity profile associated with each channel is based on a maximum Lyapunov exponent.

30. The method of claim 28, wherein the number of chaoticity profiles quantified for each channel equals the number of dimensions p being used to characterize the brain.

31. The method of claim 20, wherein said step of comparing, over time, the chaoticity profiles associated with each of the number of channel pairs comprises the step of:
   generating a T-index profile for each of the number of channel pairs based on the chaoticity profiles associated with each channel pair.

32. The method of claim 31, wherein said step of evaluating, over time, the levels of entrainment between the chaoticity profiles associated with each of the channel pairs comprises the steps of:
   comparing a sequence of T-index values associated with each T-index for each of the number of channel pairs to a T-index threshold value.

33. The method of claim 32, wherein said step of determining whether the levels of entrainment associated with one or more of the channel pairs are statistically significant comprises the step of:
   determining whether the T-index values associated with each T-index for the one or more channel pairs is less than the T-index threshold value for a given amount of time, said given amount of time and T-index threshold being selected based on a desirable level of statistical significance.

34. The method of claim 20, wherein said step of generating a seizure warning, if it is determined that the levels of entrainment associated with one or more of the channel pairs are statistically significant, comprises the step of:
   generating an impending seizure warning during a preictal stage of a next seizure.

35. The method of claim 20, wherein said step of generating a seizure warning, if it is determined that the levels of entrainment associated with one or more of the channel pairs are statistically significant, comprises the step of:
   generating a seizure susceptibility period warning during an interictal stage.

36. The method of claim 20, wherein said step of generating a seizure warning, if it is determined that the levels of entrainment associated with one or more of the channel pairs are statistically significant, comprises the step of:
   generating a time to seizure warning.

37. A method of activating a seizure interdiction device comprising the steps of:
   acquiring each of a plurality of signals from a corresponding location of a patient's brain, wherein each signal constitutes a separate channel;
   for each channel, generating a spatio-temporal response based on the corresponding signal;
   generating a chaoticity profile, comprising a sequence of chaoticity values, for each channel based on the corresponding spatio-temporal response;
   determining whether a level of entrainment between chaoticity profiles associated with a critical channel pair is statistically significant;
   generating a seizure warning if it is determined that the level of entrainment associated with the critical channel pair is statistically significant; and
   triggering the seizure interdiction device to deliver an antiseizure treatment to the patient if a seizure warning is generated.

38. The method of claim 37, wherein said step of triggering the seizure interdiction device to deliver an antiseizure treatment to the patient if a seizure warning is generated comprises the step of:
   delivering an electrical or electromagnetic stimulus to the patient's brain, vagus nerve or other neural structure to abort an impending seizure.

39. The method of claim 37, wherein said step of triggering the seizure interdiction device to deliver an antiseizure treatment to the patient if a seizure warning is generated comprises the step of:
   releasing into the patient a compound to abort an impending seizure.

40. The method of claim 37 further comprising the steps of:
   comparing the chaoticity profiles associated with a number of channel pairs;
   evaluating a level of entrainment between the chaoticity profiles associated with each of the number of channel pairs; and
   selecting one or more critical channel pairs from the number of channel pairs, wherein a critical channel pair is one which exhibits a statistically significant level of entrainment, or a maximum level of entrainment with respect to other channel pairs, during a preictal stage of a seizure.

41. The method of claim 40 further comprising the step of:
   repeating, after a seizure, the steps of evaluating a level of entrainment between the chaoticity profiles associated with each of the number of channel pairs and selecting one or more critical channel pairs from the number of channel pairs;
   updating the one or more critical channel pairs; and
   generating a seizure warning based on the level of entrainment associated with the updated one or more critical channel pairs for a next seizure.

42. The method of claim 37, wherein the sequence of chaoticity values comprise a sequence of Lyapunov exponent values.

43. The method of claim 37, wherein the seizure interdiction device is an implantable device.

44. An apparatus for providing seizure interdiction comprising:

a plurality of sensors coupled to a patient's head, said sensors detecting signals from a corresponding location of the patient's brain;

processing means for generating a seizure warning based on the plurality of signals detected by said plurality of sensors, said processing means comprising, means for receiving the plurality of signals detected by said plurality of sensors, means for preprocessing the plurality of signals detected by said sensors so as to produce a digital equivalent for each of said signals, means for generating a spatio-temporal response for each of a corresponding one of the plurality of digital signals, means for generating a chaoticity profile, comprising a sequence of chaoticity values, from each spatio-temporal response, means for determining whether a level of entrainment between chaoticity profiles associated with a critical pair of signals is statistically significant;

means for generating a seizure warning if it is determined that the level of entrainment associated with the critical signal pair is statistically significant; and a seizure interdiction device coupled to said processing means, said seizure interdiction device comprising means for delivering an antiseizure treatment to the patient if a seizure warning is generated.

45. The seizure interdiction apparatus of claim 44, wherein said seizure interdiction device is an implantable device.

46. The seizure interdiction apparatus of claim 45, wherein said implantable seizure interdiction device comprises:

means for delivering an electrical or electromagnetic stimulus to the patient's brain, vagus nerve or other neural structure to abort an impending seizure, if a seizure warning is generated.

47. The seizure interdiction apparatus of claim 45, wherein said implantable seizure interdiction device comprises:

means for releasing into the patient a drug to abort an impending seizure, if a seizure warning is generated.

* * * * *

UNITED STATES PATENT AND TRADEMARK OFFICE
CERTIFICATE OF CORRECTION

| | | |
|---|---|---|
| PATENT NO. | : 6,304,775 B1 | |
| APPLICATION NO. | : 09/400982 | |
| DATED | : October 16, 2001 | |
| INVENTOR(S) | : Iasemidis et al. | |

It is certified that error appears in the above-identified patent and that said Letters Patent is hereby corrected as shown below:

Column 1, line 6, under the second entitled "RESEARCH AND DEVELOPMENT," please replace the existing paragraph with the following:

--This invention was made with United States Government support under grant number R01 NS31451. The United States Government has certain rights in the invention.--

Signed and Sealed this
Fifteenth Day of May, 2012

David J. Kappos
*Director of the United States Patent and Trademark Office*